(12) United States Patent
Kenmoku et al.

(10) Patent No.: US 6,908,721 B2
(45) Date of Patent: Jun. 21, 2005

(54) POLYHYDROXYALKANOATE HAVING AMIDE GROUP AND SULFONIC GROUP, METHOD OF PRODUCING THE SAME, CHARGE CONTROLLING AGENT CONTAINING NOVEL POLYHYDROXYALAKNAOTE, TONER BINDER, TONER, AND IMAGE FORMING APPARATUS USING THE TONER

(75) Inventors: Takashi Kenmoku, Kanagawa (JP); Etsuko Sugawa, Kanagawa (JP); Tetsuya Yano, Kanagawa (JP); Chieko Mihara, Kanagawa (JP); Takeshi Imamura, Kanagawa (JP); Tatsuki Fukui, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/367,951

(22) Filed: Feb. 19, 2003

(65) Prior Publication Data

US 2004/0081906 A1 Apr. 29, 2004

(30) Foreign Application Priority Data

| Feb. 15, 2002 | (JP) | 2002-038399 |
| Feb. 15, 2002 | (JP) | 2002-038653 |
| Oct. 24, 2002 | (JP) | 2002-310256 |
| Jan. 23, 2003 | (JP) | 2003-014704 |

(51) Int. Cl.$^7$ ............ G03G 9/097; C08G 63/02
(52) U.S. Cl. ............ 430/108.5; 430/126; 528/271; 528/272
(58) Field of Search ............ 430/108.5, 126; 528/272, 271

(56) References Cited

U.S. PATENT DOCUMENTS

| 4,393,167 A | 7/1983 | Holmes et al. ............ 525/64 |
| 4,876,331 A | 10/1989 | Doi ............ 528/361 |
| 5,004,664 A | 4/1991 | Fuller et al. ............ 430/106.6 |
| 5,135,859 A | 8/1992 | Witholt et al. ............ 435/135 |
| 5,200,332 A | 4/1993 | Yamane et al. ............ 435/135 |
| 5,292,860 A | 3/1994 | Shiotani et al. ............ 528/361 |
| 5,667,927 A | 9/1997 | Kubota et al. ............ 430/109 |
| 6,686,439 B2 * | 2/2004 | Kenmoku et al. ............ 528/272 |
| 2003/0013841 A1 * | 1/2003 | Imamura et al. ............ 528/271 |

FOREIGN PATENT DOCUMENTS

| JP | 5-7492 | 1/1993 |
| JP | 5-93049 | 4/1993 |
| JP | 6-15604 | 3/1994 |
| JP | 6289644 | 10/1994 |
| JP | 7-14352 | 2/1995 |
| JP | 7-120975 | 5/1995 |
| JP | 7-265065 | 10/1995 |
| JP | 8-19227 | 2/1996 |
| JP | 8-262796 | 10/1996 |
| JP | 9-191893 | 7/1997 |
| JP | 2642937 | 8/1997 |
| JP | 9274335 | 10/1997 |
| JP | 9281746 | 10/1997 |
| JP | 2989175 | 12/1999 |
| JP | 178484 | 7/2001 |
| WO | WO 02-16627 | 2/2002 | ............ C12P/7/00 |

OTHER PUBLICATIONS

Helmut Ritter et al., "Bacterial Production of Polyesters Bearing Phenoxy Groups in the Side Chains, 1", Macromol. Chem. Phys., vol. 195, 1994, pp. 1665–1672.

Ohyoung Kim et al., "Bioengineering of Poly(β–hydroxyalkanoates) for Advanced Material Applications: Incorporation of Cyano and Nitrophenoxy Side Chain Substituents", Can. J. Microbiol., vol. 41, 1995, pp. 32–43.

Richard A. Gross et al., "Cyanophenoxy–Containing Microbial Polyesters: Structural Analysis, Thermal Properties, Second Harmonic Generation and In–Vivo Biodengradability", Polymer Intl., vol. 39, No. 3, 1996, pp. 205–213.

Joanne M. Curley et al., "Production of Poly(3–hydroxyalkanoates) Containing Aromatic Substituents by *Pseudomonas oleovorans*", Macromolecules, vol. 29, No. 5, 1996, pp. 1762–1766.

Won Ho Park et al., "Epoxidation of Bacterial Polyesters with Unsaturated Side Chains. I. Production and Epoxidation of Polyesters from 10–Undecenoic Acid", Macromolecules, vol. 31, 1998, pp. 1480–1486.

Won Ho Park et al., "Epoxidation of Bacterial Polyesters with Unsaturated Side Chains. II. Rate of Epoxidation and Polymer Properties", J. Polymer Sci., vol. 36, 1998, pp. 2381–2387.

(Continued)

Primary Examiner—John L Goodrow
(74) Attorney, Agent, or Firm—Fitzpatrick, Cella, Harper & Scinto

(57) ABSTRACT

A polyhydroxyalkanoate comprises a unit of formula (1): —(O—CH(($CH_2$)$_m$SASO$_2$R)$CH_2$C(=O))— wherein R is selected from the group consisting of OH, a halogen atom, ONa, OK, $OCH_3$ and $OC_2H_5$; A represents a substituted or unsubstituted aliphatic hydrocarbon structure; m is an integer number selected from 1 to 8; and in the case where a plurality of units exist in the same molecule, R, A and m in one unit can be different from them in another unit respectively. A method of producing the polyhydroxyalkanoate comprises the step of reacting a polyhydroxyalkanoate comprising a unit of formula (18): —(O—CH(($CH_2$)$_m$Br)$CH_2$C(=O))—, wherein m is an integer number selected from 1 to 8, and in the case where a plurality of units exist in the same molecule, m in one unit can be different from that in another unit, with at least one type of compounds of formula (19): HS-$A_1$-$SO_2R_{15}$ wherein $R_{15}$ is selected from the group consisting of OH, a halogen atom, ONa, OK, $OCH_3$ and $OC_2H_5$ and $A_1$ is a substituted or unsubstituted aliphatic hydrocarbon structure, and in the case where a plurality of types of compounds exist in the same molecule, $R_{15}$ and $A_1$ in one unit can be different from them in another unit respectively.

27 Claims, 8 Drawing Sheets

OTHER PUBLICATIONS

Suzette M. Aróstegui et al., "Bacterial Polyesters Produced by *Pseudomonas oleovorans* Containing Nitrophenyl Groups", Marcomolecules, vol. 32, 1999, pp. 2889–2895.

Marieta Constantin et al., "Chemical Modification of Polyhydroxyalkanoates). Copolymers Bearing Pendant Sugars", Macromol. Rapid Commun., vol. 20, 1999, pp. 91–94.

Katharina Fritzsche et al., "An Unusual Bacterial Polyester with a Phenyl Pendant Group", Makromol. Chem., 1990, pp. 1957–1965.

Y. B. Kim et al., "Preparation and Characterization of Poly(β–hydroxyalkanoates) Obtained from *Pseudomonas oleovorans* Grown with Mixtures of 5–Phenylvaleric Acid and n–Alkanoic Acids", Macromolecules, vol. 24, No. 19, 1991, pp. 5256–5260.

Bruce A. Ramsay et al., "Effect of Nitrogen Limitation on Long–Side–Chain Poly–β–Hydroxyalkanoate Synthesis by *Pseudomonas resinovorans*", Appl. and Envir. Microbiology, vol. 58, No. 2, Feb. 1992, pp. 744–746.

"Biodegradable Plastic Handbook", Biodegradable Plastic Research Associate, N.T.S. Co., Ltd., pp. 178–197 (1995).

* cited by examiner

POLYHYDROXYALKANOATE HAVING AMIDE GROUP AND SULFONIC GROUP, METHOD OF PRODUCING THE SAME, CHARGE CONTROLLING AGENT CONTAINING NOVEL POLYHYDROXYALAKNAOTE, TONER BINDER, TONER, AND IMAGE FORMING APPARATUS USING THE TONER

BACKGROUND OF THE INVENTION

1. Field of the Invention

The present invention relates to an innovative polyhydroxyalkanoate (may hereinafter be abbreviated as PHA) and a method of producing the same. Particularly, the present invention relates to a polyhydroxyalkanoate having hydrophilic groups and a method of producing the same.

In addition, the present invention relates to a charge controlling agent for use in electrophotography, electrostatic recording, magnetic recording and the like, a toner binder, an electrostatic latent image developing toner, an image formation method using the toner, and an image forming apparatus for use therein. Particularly, the present invention relates to a charge controlling agent for use in electrophotography, electrostatic recording and electrostatic printing in a copying apparatus, a printer, a facsimile machine and the like for forming an image in such a manner that a toner image is previously formed on an electrostatic latent image carrier (hereinafter, referred to simply as image carrier) and thereafter the image is transferred onto an object transfer material, a toner binder, an electrostatic latent image developing toner, an image formation method using the toner and an image forming apparatus for use therein.

2. Related Background Art

So far, many methods have been known for electrophotography, and those methods are generally carried out in such a manner that an electric latent image is formed on an image carrier (photoconductor) by a variety of means using a photoconductive substance, the latent image is then developed with a toner to form a visible image, and the toner image is transferred onto an object transfer material such as a paper as necessary, followed by fixing the toner image on the object transfer material by heat and/or pressure or the like to obtain a copy. For the method for visualizing the electric latent image, a cascade development method, a magnetic brush development method, a pressurizing development method and the like are known. Further, a method using a magnetic toner and a rotary development sleeve with a magnetic pole placed at the center thereof in which the magnetic toner is caused to fly from the development sleeve onto the photoconductor by a magnetic field is also used.

Development systems for use in development of an electrostatic latent image include a two-component development system using a two-component type developer constituted by a toner and a carrier, and a one-component development system using a one-component type developer constituted only by a toner and using no carrier.

Here, the coloring fine particle generally called as a toner has a binder resin and a coloring material as essential components, and in addition thereto, magnetic powders and the like as necessary. For the method for imparting an electric charge to the toner, the electrifiability of the binder resin itself may be used without using a charge controlling agent, but in this method, charge stability with time and humidity resistance are compromised, thus making it impossible to obtain high quality images. Therefore, the charge controlling agent is usually added for the purpose of maintaining and controlling the charge of the toner.

Today, charge controlling agents known in the art include, for example, azo dye metal complexes, aromatic dicarboxylic-metal complexes and salicylic acid derivative-metal complexes for the negative friction charging agent. In addition, for the positive friction charging agent, nigrosine based dyes, triphenylmethane based dyes, various kinds of quaternary ammonium salts, and organic tin compounds such as dibutyl tin oxide are known, but toners containing these substances as the charge controlling agent do not necessarily fully satisfy quality characteristics required for the toner such as the electrifiability and stability with time depending on their compositions.

For example, a toner containing an azo dye metal complex known as a negative charge controlling agent has an acceptable charge level, but may have reduced dispersibility depending on the type of binder resin to be combined because the azo dye metal complex is a low-molecular crystal. In this case, the negative charge controlling agent is not uniformly distributed in the binder resin, the charge level distribution of the obtained toner is significantly lacking in sharpness, and the obtained image has a low gray-level, resulting in a poor image formation capability. In addition, the azo dye metal complex has a unique color tone, and is thus presently used only for toners having limited colors around black, and if the azo dye metal complex is used as a color toner, its lack in clarity as a coloring agent required for obtaining an image having a high level of requirement for the color tone is a serious problem.

In addition, examples of almost colorless negative charge controlling agents include aromatic dicarboxylic-acid metal complexes, but they may be disadvantageous due to the fact that they are not perfectly colorless, and that they have low dispersibility peculiar to low-molecular-weight crystals.

On the other hand, nigrosine based dyes and triphenylmethane based dyes are presently used only for toners having limited colors around black because they are colored themselves, and may be poor in time stability of toners for continuous copying. In addition, conventional quaternary ammonium salts may have insufficient humidity resistance when formed into toners, and in this case, the stability with time may be so poor that high quality images are not provided as they are repeatedly used.

In addition, in recent years, attention has been given worldwide to reduction of wastes and improvement of safety of wastes in terms of environmental protection. This problem applies to the field of electrophotography as well. That is, as imaging apparatuses have been widely used, the amounts of wastes of printed papers, discarded toners and copying papers have increased year by year, and the safety of such wastes is important from a viewpoint of protection of global environment.

Polyhydroxyalkanoate (PHA)

Resins that can be decomposed with time by the action of microorganisms and the like, namely biodegradable resins are under development in terms of environmental protection, and for example, many types of microorganism have been reported to produce biodegradable resins having polyester structures (polyhydroxyalkanoate: hereinafter abbreviated as PHA) and accumulate the resin in the cell (Non-patent Document 1). These polymers may be used for production of various kinds of products through melt processing as in the case of conventional plastics. In addition, these polymers have an advantage that owing to their biodegradability, they are fully decomposed by microorganism in the natural environment, and unlike many synthetic polymer compounds, they never remain in the natural environment to cause contamination. In addition, they are also excellent in biocompatibility, and are expected to be applied as medical flexible members and the like.

It is known that such PHA may various compositions and structures depending on the type of microorganism to be used for the production of the PHA, the culture medium composition and the culture condition, and hitherto studies have been conducted mainly on control of the composition and structure of PHA to be produced in terms of improvements of properties of PHA.

[1] First, the biosynthesis of PHA obtained by polymerizing a monomer unit with a relatively simple structure such as 3-hydroxybutyric acid (hereinafter abbreviated as 3HB) is exemplified as follows:

(a) those containing 3HB and 3-hydroxyvaleric acid (hereinafter abbreviated as 3HV) (see Patent Documents 1 to 4);

(b) those containing 3HB and 3-hydroxyhexanoic acid (hereinafter abbreviated as 3HHx) (see Patent Documents 5 and 6);

(c) those containing 3HB and 4-hydroxybutyric acid (hereinafter abbreviated as 4HB) (see Patent Document 7);

(d) those containing 3-hydroxyalkanoate having 6 to 12 carbon atoms (see Patent Document 8); and (e) biosynthesis using a single aliphatic acid as a carbon source (the resulting product is almost same as those of (d)) (see Non-Patent Document 2).

They are all PHA composed of monomer units each having an alkyl group in the side chain, synthesized by β-oxidation of hydrocarbons and the like or synthesis of fatty acid from saccharides by microorganism, namely "usual PHA".

Such PHA has already found considerable applications with proven performance particularly in the field of agriculture, the biodegradable resin is used in mulch files, horticulture materials, slow-releasable agricultural chemicals, fertilizers and the like. Also, in the leisure industry, the biodegradable resin is used in fishing lines, fishing tackles, golf requites and the like.

[2] However, if considering a wide range of application as a plastic, it cannot be the above described that PHA is fully usable in terms of properties in the present situation. For further expanding the range of application of PHA, it is important to conduct a wide range of studies on the improvement of properties, and for this purpose, development and search of PHA including monomer units of a variety of structures is prerequisite. On the other hand, PHA with a substituent group introduced in the side chain ("unusual PHA") can be expected to be developed as a "functional polymer" with very useful functions and properties originating from the introduced substituent group by selecting the introduced substituent group according to desired characteristics and the like. That is, it is also an important challenge to conduct of development and search of excellent PHA enabling such functionality and biodegradability to be compatible with each other. Examples of substituent groups include groups containing aromatic rings (phenyl group, phenoxy group, etc.), unsaturated hydrocarbons, ester groups, allyl groups, cyano groups, halogenated hydrocarbons and epoxide. Among them, studies on PHA having an aromatic ring are particularly vigorously conducted.

(a) PHA Containing a Phenyl Group or its Partially Substituted Group

It is reported that Pseudomonas oleovorans produces PHA containing 3-hydroxy-5-phenylvaleric acid as a unit using 5-phenylvaleric acid as a substrate (see Non-Patent Documents 3 and 4).

It is reported that Pseudomonas oleovorans produces PHA containing 3-hydroxy-5-(4'-tolyl) valeric acid as a unit using 5-(4'-tolyl) valeric acid as a substrate (see Non-Patent Document 5).

It is reported that Pseudomonas oleovorans produces PHA containing 3-hydroxy-5-(2',4'-dinitrophenyl) valeric acid and 3-hydroxy-5-(4'-nitrophenyl) valeric acid as a unit using 5-(2',4'-dinitrophenyl) valeric acid as a substrate (see Non-Patent Document 6).

(b) PHA Containing a Phenoxy Group or its Partially Substituted Group

It is reported that Pseudomonas oleovorans produces a PHA copolymer of 3-hydroxy-5-phenoxyvaleric acid and 3-hydroxy-9-phenoxynonanoic acid using 11-pheoxyundecanoic acid as a substrate (see Non-Patent Document 7).

An invention relating to a homopolymer consisting of 3-hydroxy-5-(monofluorophenoxy) pentanoate (3H5(MFP)P) units or 3-hydroxy-5-(difluorophenoxyl) pentanoate (3H5(DFP)P) units, a copolymer containing at least (3H5(MFP)P) units or (3H5(DFP)P) units; *Pseudomonas putida* synthesizing these polymers; and a method of producing the above described polymers using *Pseudomonas* species is disclosed, and it is described that as an advantage of the above invention, a long chain aliphatic acid having substituent groups can be metabolized to synthesize a polymer having a phenoxy group substituted with 1 or 2 fluorine atoms at the side chain terminal, and stereoregularity and water repellency are provided while maintaining a high melting point and good processability (see Patent Document 9).

Studies are conducted on cyano-substituents and nitro-substituents in addition to the fluorine-substituent described above.

It is reported that PHA containing 3-hydroxy-p-cyanophenoxyhexanoic acid or 3-hydroxy-p-nitrophenoxyhexanoic acid as a monomer unit is produced with octanoic acid and p-cyanophenoxyhexanoic acid or p-nitrophenoxyhexanoic acid as substrates using a Pseudomonas oleovorans ATCC 29347 strain and a *Pseudomonas putida* KT 2442 strain (see Non-Patent Documents 8 and 9).

These reports are useful in obtaining polymers each having an aromatic ring in the side chain of PHA and having properties derived therefrom unlike general PHA whose side chain contains an alkyl group.

[3] In addition, as a new category, studies are conducted for producing PHA having an appropriate functional group in the side chain and using the functional group to create a new function, beyond mere modification of properties of PHA.

It is reported that PHA containing a unit having a vinyl group at the terminal of the side chain was synthesized, and was thereafter epoxidized, whereby PHA containing a highly reactive epoxy group at the side chain terminal could be synthesized (see Non-Patent Documents 10 and 11).

In addition, it is reported that PHA containing a unit having a vinyl group at the terminal of the side chain was synthesized, and thereafter benzoyl peroxide was used with per-O-acetyl-1-thio-β-maltose, whereby PHA containing a sugar chain could be synthesized, and that PHA containing a unit having a bromo group at the terminal of the side chain was synthesized, and thereafter diethyl amine was used with per-O-acetyl-1-thio-β-maltose, whereby PHA containing a sugar chain could be synthesized (see Non-Patent Document 12).

Application of Biodegradable Resin to Toner

Application of a biodegradable resin to a binder resin particularly in production of toners is proposed in the field of electrophotography as well. For example, U.S. Pat. No. 5,004,664 (Patent Document 10) discloses a toner having as its composition a biodegradable resin, particularly polyhydroxy butyric acid and polyhydroxy valeric acid, a copolymer thereof or a blend thereof. In addition, Japanese Patent Application Laid-Open No. 6-289644 (Patent Document 11) discloses an electrophotographic toner particularly for heated roll fixation characterized in that at least the binder resin contains a plant based wax and a biodegradable resin (e.g. polyester produced by microorganism, and natural polymer material of plant or animal origin), and the above described plant based wax is added in the above described binder in an amount of 5 to 50% by weight.

In addition, Japanese Patent Application Laid-Open No. 7-120975 (Patent Document 12) discloses an electrophotographic toner characterized by containing a lactic acid based resin as a binder resin. In addition, Japanese Patent Application Laid-Open No. 9-274335 (Patent Document 13) discloses an electrostatic latent image developing toner characterized by containing a polyester resin obtained by dehydrating polycondensation of a composition containing lactic acid and tri- or higher functional oxycarboxylic acid and a coloring agent.

In addition, Japanese Patent Application Laid-Open No. 8-262796 (Patent Document 14) discloses an electrophotographic toner containing a binder resin and a coloring agent, characterized in that the binder resin is composed of a biodegradable resin (e.g. aliphatic polyester resin), and the coloring agent is composed of non-water soluble pigments. In addition, Japanese Patent Application Laid-Open No. 9-281746 (Patent Document 15) discloses an electrostatic latent image developing toner characterized by containing an urethane-modified polyester resin obtained by cross-linking polylactic acid with a tri- or higher functional polyvalent isocyanate and a coloring agent.

Any one of the above described electrophotographic toners contains a biodegradable resin as binder resin, and is regarded to be effective to contribute to preservation of environments and the like.

However, reports of examples of using a biodegradable resin in the charge controlling agent have not been known, and there is a room for further improvement for contribution to preservation of environments.

In addition to the above described documents, the content of Japanese Patent Application Laid-Open No. 2001-178484 (Patent Document 16) is herein incorporated.

[Patent Document 1] Japanese Patent Publication No. 6-15604

[Patent Document 2] Japanese Patent Publication No. 7-14352

[Patent Document 3] Japanese Patent Publication No. 8-19227

[Patent Document 4] Japanese Patent Application Laid-Open No. 5-7492

[Patent Document 5] Japanese Patent Application Laid-Open No. 5-93049

[Patent Document 6] Japanese Patent Application Laid-Open No. 7-265065

[Patent Document 7] Japanese Patent Application Laid-Open No. 9-191893

[Patent Document 8] Japanese Patent No. 2642937

[Patent Document 9] Japanese Patent No. 2989175

[Patent Document 10] U.S. Pat. No. 5,004,664

[Patent Document 11] Japanese Patent Application Laid-Open No. 6-289644

[Patent Document 12] Japanese Patent Application Laid-Open No. 7-120975

[Patent Document 13] Japanese Patent Application Laid-Open No. 9-274335

[Patent Document 14] Japanese Patent Application Laid-Open No. 8-262796

[Patent Document 15] Japanese Patent Application Laid-Open No. 9-281746

[Patent Document 16] Japanese Patent Application Laid-Open No. 2001-178484

[Non-Patent Document 1] "Biodegradable Plastic Handbook" Biodegradable Plastic Research Associate, N.T.S. Co., Ltd., p. 178–197 (1995)

[Non-Patent Document 2] Appl. Environ. Microbiol, 58 (2), p. 746 (1992)

[Non-Patent Document 3] Makromol. Chem., 191, p. 1957–1965 (1990).

[Non-Patent Document 4] Macromolecules, 24, p. 5256–5260 (1991)

[Non-Patent Document 5] Macromolecules, 29, p. 1762–1766 (1996)

[Non-Patent Document 6] Macromolecules, 32, p. 2889–2895 (1999)

[Non-Patent Document 7] Macromol. Chem. Phys., 195, p. 1665–1672 (1994)

[Non-Patent Document 8] Can. J. Microbiol., 41, p. 32–43 (1995)

[Non-Patent Document 9] Polymer International, 39, p. 205–213 (1996)

[Non-Patent Document 10] Macromolecules, 31, p. 1480–1486 (1996)

[Non-Patent Document 11] Journal of Polymer Science: Part A: Polymer Chemistry, 36, p. 2381–2387 (1998)

[Non-Patent Document 12] Macromol. Rapid Commun., 20, p. 91–94 (1999)

As described above, researches are being conducted for creating a new function, but only few successful cases have been reported. In particular, 3-hydroxybutylic acid has an advantage that it is completely decomposed by microorganism in the nature, but it has a problem in terms of melt processability because of its high crystallinity, hardness and fragility. Therefore, PHA with improved melt processability has been desired.

SUMMARY OF THE INVENTION

An object of the present invention is to provide an innovative polyhydroxyalkanoate with sulfonic group as a hydrophilic group or a derivative thereof introduced for improving melt processability, and a method of producing the same. In addition, the polyhydroxyalkanoate of the present invention is excellent in biocompatibility owing to its hydrophilic nature, and is expected to be applied as medical flexible members and the like.

In addition, for solving the above described problems, the present invention provides a negatively charged charge controlling agent being more contributable to preservation of environments and the like, and having high performance (high charge level, quick start of charge, excellent stability with time, and high environmental stability) and improved dispersibility in the aspect of functionality, a toner binder containing the charge controlling agent, an electrostatic latent image developing toner containing the charge controlling agent, and an image formation method and an image forming apparatus using the electrostatic latent image developing toner.

Thus, the inventors have devised the following invention as a result of vigorously conducting researches for development of an innovative polyhydroxyalkanoate with a hydrophilic group introduced, which is believed to be useful for improving melt processability. In addition, the inventors have vigorously conducted studies for developing a charge controlling agent having high performance and being substantially colorless, resulting in the achievement of the present invention.

That is, the outline of the present invention is as follows.

[1] A polyhydroxyalkanoate comprising a unit of formula (1):

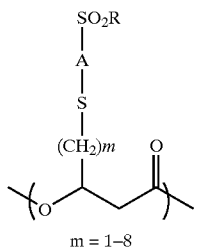

(1)

$m = 1-8$ wherein R is selected from the group consisting of OH, a halogen atom, ONa, OK, $OCH_3$ ane $OC_2H_5$; A represents a substituted or unsubstituted aliphatic hydrocarbon structure; m is an integer number selected from 1 to 8; and in the case where a plurality of units exist in the same molecule, R, A and m in one unit can be different from them in another unit respectively.

[2] The polyhydroxyalkanoate according to item [1], comprising a unit of formula (2):

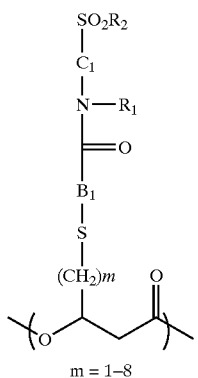

(2)

$m = 1-8$ wherein $R_1$ is H or $CH_3$; $R_2$ is selected from the group consisting of OH, a halogen atom, ONa, OK, $OCH_3$ and $OC_2H_5$; $B_1$ and $C_1$ each represent a substituted or unsubstituted aliphatic hydrocarbon structure; m is an integer number selected from 1 to 8; and in the case where a plurality of units exist in the same molecule, $R_1$, $R_2$, $B_1$, $C_1$ and m in one unit can be different from them in another unit respectively.

[3] The polyhydroxyalkanoate according to item [2], comprising a unit of formula (3):

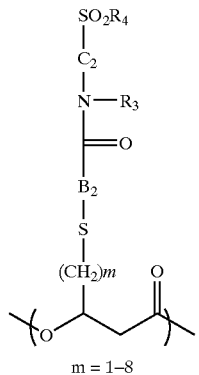

(3)

$m = 1-8$ wherein $R_3$ is H or $CH_3$; $R_4$ is selected from the group consisting of OH, a halogen atom, ONa, OK, $OCH_3$ and $OC_2H_5$; $B_2$ and $C_2$ each represent a straight-chain or branched alkylene group having 1 to 8 carbon atoms; m is an integer number selected from 1 to 8; and in the case where a plurality of units exist in the same molecule, $R_3$, $R_4$, $B_2$, $C_2$ and m in one unit can be different from them in another unit respectively.

[4] The polyhydroxyalkanoate according to item [3], comprising a unit of formula (4):

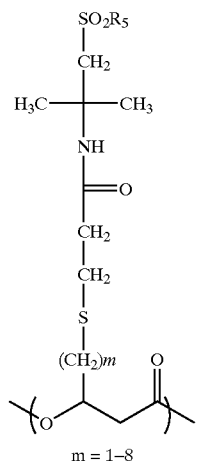

(4)

$m = 1-8$ wherein $R_5$ is selected from the group consisting of OH, a halogen atom, ONa, OK, $OCH_3$ and $OC_2H_5$; m is an integer number selected from 1 to 8; and in the case where a plurality of units exist in the same molecule, $R_5$ and m in one unit can be different from them in another unit respectively.

[5] The polyhydroxyalkanoate according to item [1], wherein m in formula (1) is an integer selected from the group consisting of 4, 6 and 8.

[6] The polyhydroxyalkanoate according to item [1], wherein m in formula (1) is an integer of 3 or 5.

[7] The polyhydroxyalkanoate according to item [1], comprising at least one of
a 3-hydroxy-ω-alkanoic acid unit of formula (5):

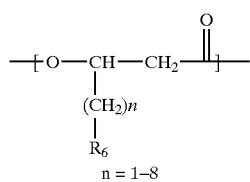

(5)

n = 1–8 wherein n is an integer number selected from 1 to 8; $R_6$ contains a residue having a phenyl structure or a thienyl structure; and in the case where a plurality of units exist in the same molecule, n and $R_6$ in one unit can be different from them in another unit respectively and
a 3-hydroxy-ω-cyclohexylalkanoic acid unit of formula (6):

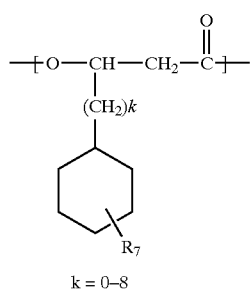

(6)

k = 0–8 wherein $R_7$ is a substituent group in the cyclohexyl group selected from the group consisting of H, CN, $NO_2$, a halogen atom, $CH_3$, $C_2H_5$, $C_3H_7$, $CF_3$, $C_2F_5$ and $C_3F_7$; k is an integer number selected from 0 to 8; and in the case where a plurality of units exist in the same molecule, k and $R_7$ in one unit can be different from them in another unit respectively.

[8] The polyhydroxyalkanoate according to item [7], wherein $R_6$ in formula (5) is selected from the group consisting of the groups of the following formulas (7), (8), (9), (10), (11), (12), (13), (14), (15), (16) and (17):
unsubstituted or substituted phenyl groups of formula (7):

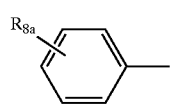

(7)

wherein $R_{8a}$ represents a substituent group in the aromatic ring selected from the group consisting of H, a halogen atom, CN, $NO_2$, $CH_3$, $C_2H_5$, $C_3H_7$, $CH=CH_2$, $COOR_{8b}$ ($R_{8b}$ represents any one selected from the group consisting of H, Na and K), $CF_3$, $C_2F_5$ and $C_3F_7$, and in the case where a plurality of units exist in the same molecule, $R_{8a}$ in one unit can be different from that in another unit;
unsaturated or saturated phenoxy groups of formula (8):

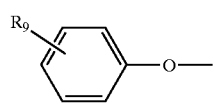

(8)

wherein $R_9$ represents a substituent group in the aromatic ring selected from the group consisting of H, a halogen atom, CN, $NO_2$, $CH_3$, $C_2H_5$, $C_3H_7$, $SCH_3$, $CF_3$, $C_2F_5$ and $C_3F_7$, and in the case where a plurality of units exist in the same molecule, $R_9$ in one unit can be different from that in another unit;
unsubstituted or substituted benzoyl groups each of formula (9):

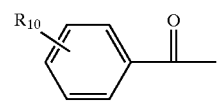

(9)

wherein $R_{10}$ represents a substituent group in the aromatic ring selected from the group consisting of H, a halogen atom, CN, $NO_2$, $CH_3$, $C_2H_5$, $C_3H_7$, $CF_3$, $C_2F_5$ and $C_3F_7$, and in the case where a plurality of units exist in the same molecule, $R_{10}$ in one unit can be different from that in another unit;
unsubstituted or substituted phenylsulfanyl groups of formula (10):

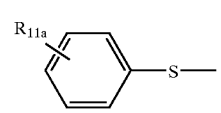

(10)

wherein $R_{11a}$ represents a substituent group in the aromatic ring selected from the group consisting of H, a halogen atom, CN, $NO_2$, $COOR_{11b}$, $SO_2R_{11c}$ ($R_{11b}$ represents any one selected from the group consisting of H, Na, K, $CH_3$ and $C_2H_5$, and $R_{11c}$ represents any one selected from the group consisting of OH, ONa, OK, a halogen atom, $OCH_3$ and $OC_2H_5$), $CH_3$, $C_2H_5$, $C_3H_7$, $(CH_3)_2$—CH and $(CH_3)_3$—C, and in the case where a plurality of units exist in the same molecule, $R_{11a}$ in one unit can be different from that in another unit;
unsubstituted or substituted (phenylmethyl) sulfanyl groups of formula (11):

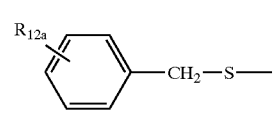

(11)

wherein $R_{12a}$ represents a substituent group in the aromatic ring selected from the group consisting of H, a halogen atom, CN, $NO_2$, $COOR_{12b}$, $SO_2R_{12c}$ ($R_{12b}$ represents any one selected from the group consisting of H, Na, K, $CH_3$ and $C_2H_5$, and $R_{12c}$ represents any one selected from the group consisting of OH, ONa, OK, a halogen atom, $OCH_3$ and $OC_2H_5$), $CH_3$, $C_2H_5$, $C_3H_7$, $(CH_3)_2$—CH and $(CH_3)_3$—C, and in the case where a plurality of units exist in the same molecule, $R_{12a}$ in one unit can be different from that in another unit;
2-thienyl group of formula (12):

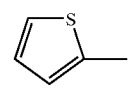

(12)

2-thienylsulfanyl group of formula (13):

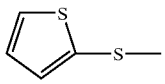
(13)

2-thienylcarbonyl group of formula (14):

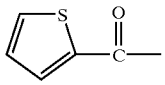
(14)

unsubstituted or substituted phenylsulfinyl groups of formula (15):

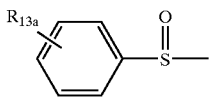
(15)

wherein $R_{13a}$ represents a substituent group in the aromatic ring selected from the group consisting of H, a halogen atom, CN, $NO_2$, $COOR_{13b}$ ($R_{13b}$ represents any one selected from the group consisting of H, Na, K, $CH_3$ and $C_2H_5$), $SO_2R_{13c}$ ($R_{13c}$ represents any one selected from the group consisting of OH, ONa, OK, a halogen atom, $OCH_3$ and $OC_2H_5$), $CH_3$, $C_2H_5$, $C_3H_7$, $(CH_3)_2$—CH and $(CH_3)_3$—C, and in the case where a plurality of units exist in the same molecule $R_{13a}$ in one unit can be different from that in another unit;

unsubstituted or substituted phenylsulfonyl groups of formula (16):

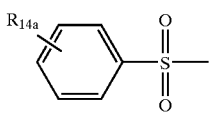
(16)

wherein $R_{14a}$ represents a substituent group in the aromatic ring selected from the group consisting of H, a halogen atom, CN, $NO_2$, $COOR_{14b}$ ($R_{14b}$ represents any one selected from the group consisting of H, Na, K, $CH_3$ and $C_2H_5$), $SO_2R_{14b}$ ($R_{14c}$ represents any one selected from the group consisting of OH, ONa, OK, a halogen atom, $OCH_3$ and $OC_2H_5$), $CH_3$, $C_2H_5$, $C_3H_7$, $(CH_3)_2$—CH and $(CH_3)_3$—C, and in the case where a plurality of units exist in the same molecule $R_{14a}$ in one unit can be differend from that in another unit; and (phenylmethyl)oxy groups of formula (17):

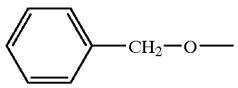
(17)

, and in the case where a plurality of units exist in the same molecule, $R_6$ in one unit of formula (5) can be different from that in another unit.

[9] The polyhydroxyalkanoate according to item [1], wherein the number-average molecular weight is in the range of from 1000 to 1000000.

[10] A method of producing polyhydroxyalkanoate comprising a unit of formula (1), which comprises the step of:

reacting a polyhydroxyalkanoate comprising a unit of formula (18):

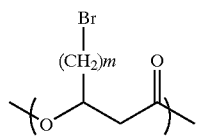
(18)

, wherein m is an integer number selected from 1 to 8, and in the case where a plurality of units exist in the same molecule, m in one unit can be different from that in another unit,
with at least one type of compounds of formula (19):

$$HS\text{-}A_1\text{-}SO_2R_{15} \quad (19)$$

wherein $R_{15}$ is selected from the group consisting of OH, a halogen atom, ONa, OK, $OCH_3$ and $OC_2H_5$ and $A_1$ is a substituted or unsubstituted aliphatic hydrocarbon structure, and in the case where a plurality of types of compounds exist in the same molecule, $R_{15}$ and $A_1$ in one unit can be different from them in another unit respectively.

[11] A method of producing polyhydroxyalkanoate comprising a unit of formula (2), which comprises the step of:
reacting a polyhydroxyalkanoate comprising a unit of formula (18) with at least one type of compounds of formula (20):

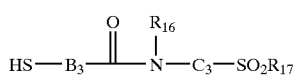
(20)

wherein $R_{16}$ is H or $CH_3$; $R_{17}$ is selected from the group consisting of OH, a halogen atom, ONa, OK, $OCH_3$ and $OC_2H_5$; $B_3$ and $C_3$ are selected from substituted or unsubstituted aliphatic hydrocarbon structures; and in the case where a plurality of types of compounds exist in the same molecule, $R_{16}$, $R_{17}$, $B_3$ and $C_3$ in one unit can be different from them in another unit respectively.

[12] The method according to item [10], wherein the reacting step is carried out under basic condition.

[13] The method according to item [12], wherein at least one selected from the group consisting of dimetylamine, diethylamine, trimethylamine, triethylamine, dibutylamine, morpholine, piperidine, sodium hydride, sodium hydroxide, potassium hydroxide, sodium carbonate, potassium carbonate, sodium methylate and sodium ethylate is used as a basic catalyst in the reacting step.

[14] A charge controlling agent controlling the charged state of powder, the charge controlling agent containing polyhydroxyalkanoate comprising a unit of formula (1).

[15] The charge controlling agent controlling the charged state of powder according to item [14], the charge controlling agent containing polyhydroxyalkanoate comprising a unit of formula (2).

[16] The charge controlling agent controlling the charged state of powder according to item [15], the charge controlling agent containing polyhydroxyalkanoate comprising a unit of formula (3).

[17] The charge controlling agent controlling the charged state of powder according to item [16], the charge controlling agent containing polyhydroxyalkanoate comprising a unit of formula (4).

[18] The charge controlling agent according to item [14], comprising at least one of a 3-hydroxy-ω-alkanoic acid unit of formula (5) and a 3-hydroxy-ω-cyclohexylalkanoic acid unit of formula (6).

[19] The charge controlling agent according to item [18], wherein $R_6$ in chemical formula (5) is selected from the group consisting of formulae (7), (8), (9), (10), (11), (12), (13), (14), (15), (16) and (17).

[20] The charge controlling agent according to item [14], wherein the powder is an electrostatic latent image developing toner.

[21] The charge controlling agent according to item [14], wherein the number-average molecular weight of the polyhydroxyalkanoate is in the range of from 1000 to 1000000.

[22] A toner binder for use in an electrostatic latent image developing toner, the toner binder containing the charge controlling agent according to item [14].

[23] An electrostatic latent image developing toner containing a binder resin, a coloring agent and the charge controlling agent according to item [14].

[24] A method for forming an image which comprises the steps of:
applying a voltage to an electrification member from the outside to electrify an electrostatic latent image carrier,
forming an electrostatic latent image on the electrified electrostatic latent image carrier,
developing the electrostatic latent image by an electrostatic latent image developing toner to form a toner image on the electrostatic latent image carrier,
transferring the toner image on the electrostatic latent image carrier to a record material, and
fixing the toner image on the record material by heat, wherein an electrostatic latent image developing toner according to item [23] is used.

[25] The method according to item [24], wherein the transferring step comprises a first transferring step of transferring the toner image on the electrostatic latent image carrier to an intermediate transfer body and a second transferring step of transferring the toner image on the intermediate transfer body to the record material.

[26] An image forming apparatus comprising a means for applying a voltage to an electrification member from the outside to electrify an electrostatic latent image carrier, a means for forming an electrostatic latent image on the electrified electrostatic latent image carrier, a means for developing the electrostatic latent image by an electrostatic latent image developing toner to form a toner image on the electrostatic latent image carrier, a means for transferring the toner image on the electrostatic latent image carrier to a record material, and a means for fixing the toner image on the record material by heat, wherein an electrostatic latent image developing toner according to item [23] is used.

[27] The image forming apparatus according to item [26], wherein the transferring means comprises a first transferring means for transferring the toner image on the electrostatic latent image carrier to an intermediate transfer body and a second transferring means for transferring the toner image on the intermediate transfer body to the record material.

DETAILED DESCRIPTION OF THE PREFERRED EMBODIMENTS

Figure 1:
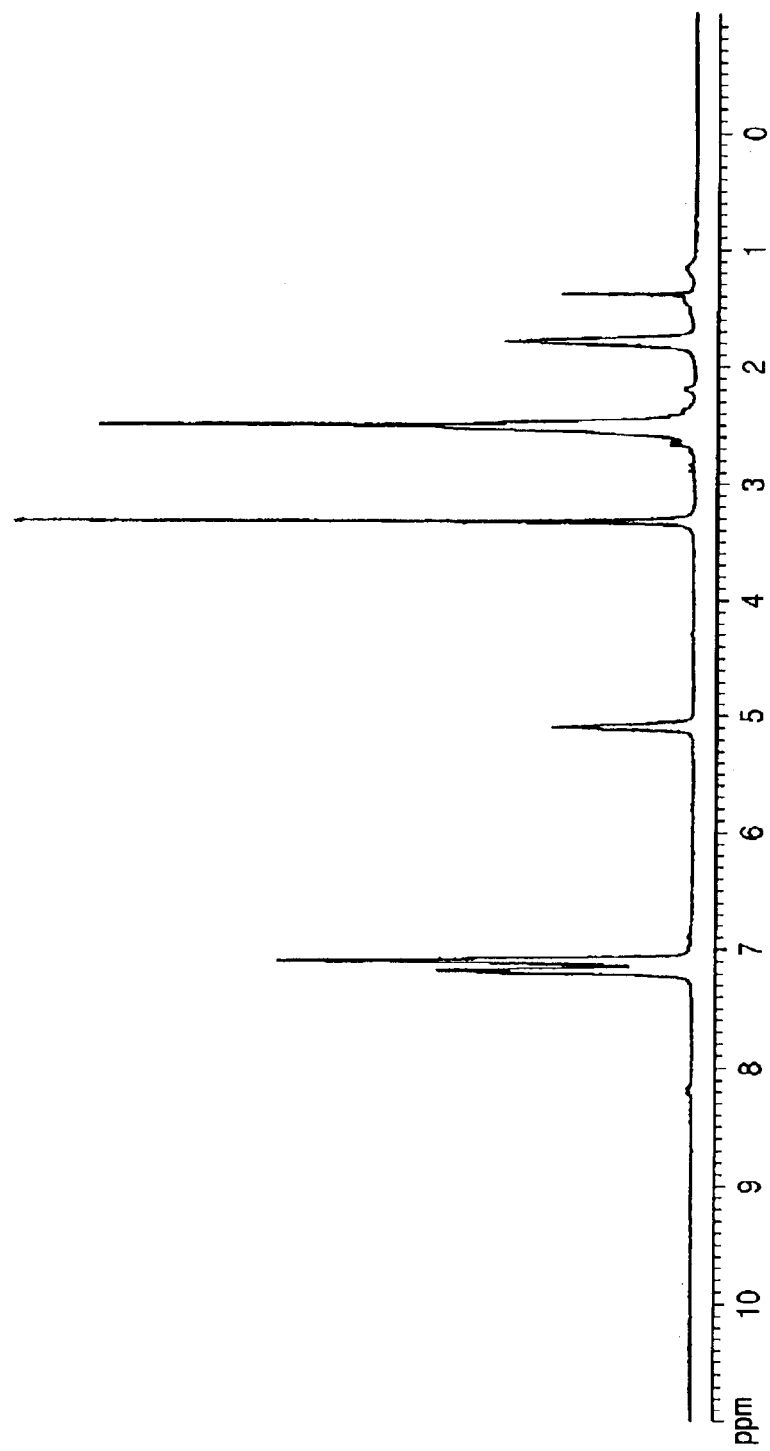
FIG. 1 shows a $^1$H-NMR spectrum chart of polyhydroxyalkanoate (PHA) produced in Example 1.

The compound for use in the present invention has a basic skeleton as a biodegradability resin, and is therefore capable of being used for producing various kinds of products through melt-processing and the like as in the case of conventional plastics, and also has a remarkable characteristic such that it is decomposed by microorganism and involved in the material cycle in the natural world unlike synthetic polymers derived from oil.

The compound presented in the present invention, which is suitable as a charge controlling agent for use in an electrostatic latent image developing toner of the present invention will specifically be described. The compound for use in the present invention is a polyester resin having 3-hydroxyalkanoate as a monomer unit, namely polyhydroxyalkanoate having units each expressed by chemical formula (1).

Here, when such a compound is produced by a method comprising a step of producing the compound by microorganism, the compound presented in the present invention is an isotactic polymer composed only of a R configuration, but is not particularly limited to the isotactic polymer and can be used for an atactic polymer as long as the object of the present invention can be achieved in terms of both properties and functions.

The polyhydroxyalkanoate of chemical formula (1) desired in the present invention is produced by a reaction between polyhydroxyalkanoate containing 3-hydroxy-ω-bromoalkanoic acid units each expressed by chemical formula (18), which is used as a starting material, and at least one type of compound expressed by chemical formula (19).

[Method of Producing Polyhydroxyalkanoate Containing Units Each Expressed by Chemical Formula (18)]

The polyhydroxyalkanoate containing units each expressed by chemical formula (18) for use in the present invention can be produced using, but not limited to, a method of production by microorganism, a method of production by a gene-manipulated plant crop system and a method of production by chemical polymerization. Preferably, the method of production by microorganism is used.

A method of producing polyhydroxyalkanoate containing units each expressed by chemical formula (18) in the present invention in which microorganism is used will be described in detail.

If the production by microorganism in the present invention is used, any microorganism may be used as long as it is capable of producing a polyhydroxyalkanoate containing units each expressed by chemical formula (18) when cultured in a culture medium containing at least one type of compound expressed by chemical formula (21), and one example thereof is a microorganism belonging to the *Pseudomonas* genus.

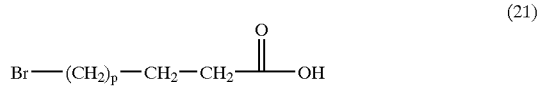

(21)

(In the formula, p is an integer number selected from 1 to 8.)

More particularly, the microorganism includes *Pseudomonas cichorii* YN2 (FERM BP-7375), *Pseudomonas cichorii* H45 (FERM BP-7374), *Pseudomonas jessenii* P161 (FERM BP-7376) and *Pseudomonas putida* P91 (FERM BP-7373). These four types of microorganisms are deposited at International Patent Organism Depositary, National Institute of Advanced Industrial Science and Technology (former National Institute of Bioscience and Human-Technology, Agency of Industrial Science and Technology) and described in Japanese Patent Laid-Open No. 2001-178484 (Patent Document 16).

These microorganisms are capable of producing PHA containing a corresponding ω-substituted-3-hydroxyalkanoic acid as a monomer unit using as a raw material a ω-substituted-straight chain alkanoic acid substituted at the chain terminal with a six-membered ring atom group selected from the group consisting of a substituted or unsubstituted phenyl group, a substituted or unsubstituted phenoxy group and a substituted or unsubstituted cyclohexyl group, or a ω-substituted-straight chain alkanoic acid substituted at the chain terminal with a five-membered ring atom group such as a thienyl group.

(Culture Process)

For usual culture of a microorganism for use in the method of producing PHA according to the present invention, for example, production of preservation strains and propagation to secure the number of cells and the level of activity required for production of PHA, a culture medium containing components required to propagate the microorganism to be used is appropriately selected. For example, as long as the growth and survival of microorganisms is not adversely affected, any type of culture medium such as a general natural medium (bouillon medium, yeast extract, etc.) and a synthetic medium with a nutrient source added therein may be used. Culture conditions including among other things temperature, ventilation and agitation conditions may be selected as appropriate depending on the type of microorganism to be used.

In the production method of the present invention, any culture medium may be used for the culture medium for use in the process of culturing a microorganism as long as the culture medium is an inorganic salt culture medium containing a phosphate and a nitrogen source such as an ammonium salt or nitrate, and in the process of producing PHA in the microorganism, the productivity of PHA can be improved by adjusting the concentration of the nitrogen source.

In addition, nutrients such as an yeast extract, polypeptone and a meat extract can be added to the culture medium as a matrix for, promoting the propagation of the microorganism. That is, peptides may be added as an energy source and a carbon source in the form of nutrients such as an yeast extract, polypeptone and a meat extract.

Alternatively, for the culture medium, saccharides, for example, aldoses such as glyceroaldehyde, erythrose, arabinose, xylose, glucose, galactose, mannose and fructose, alditols such as glycerol, erythritol and xylitol, aldonic acids such as gluconic acid, uronic acids such as glucuronic acid and galacturonic acid, and disaccharides such as maltose, sucrose and lactose may be used as an energy source and a carbon source consumed with propagation of the microorganism.

Instead of the above described saccharides, organic acids or salts thereof, more specifically organic acids involved in the TCA cycle and organic acids derived from a biochemical reaction with less steps by one or two steps than the TCA cycle, or water soluble salts thereof may be used. As the organic acid or salt thereof, hydroxycarboxylic acids and oxocarboxylic acids such as pyruvic acid, oxalacetic acid, citric acid, isocitric acid, ketoglutaric acid, succinic acid, fumaric acid, malic acid and lactic acid or water soluble salts thereof can be used. Alternatively, amino acids or salts thereof, for example amino acids such as asparaginic acid and glutamic acid or salts thereof can be used. When the organic acid or salt thereof is added, it is more preferable that one or more types are selected from a group consisting of pyruvic acid, oxalacetic acid, citric acid, isocitric acid, ketoglutaric acid, succinic acid, fumaric acid, malic acid, lactic acid and salts thereof, and are added to the culture medium and dissolved therein. Alternatively, when the amino acid or salt thereof is added, it is more preferable that one or more types are selected from a group consisting of asparaginic acid, glutamic acid and salts thereof, and are added to the culture medium and dissolved therein. At this time, as required, all or part thereof can be added in the form of a water soluble salt to be dissolved uniformly without affecting the pH of the culture medium.

It is desirable that the concentration of the above coexisting substrate added to the culture medium as a carbon source for growth of the microorganism and energy source for production of PHA is usually selected so that it is in the range of from 0.1 to 5% (w/v), more preferably 0.2 to 2% (w/v) per culture medium. That is, for peptides, yeast extracts, organic acids or salts thereof, amino acids or salts thereof, and saccharides that are used as the above coexisting substrates, one or more types thereof may be added, and at this time, it is desirable that the total concentration of these added substrates is with in the above described range of total concentrations.

It is desirable that the content of the matrix for production of desired PHA, namely the compound expressed by general formula (21) is selected so that it is in the range of from 0.0005 to 1% (w/v), more preferably 0.001 to 0.2% (w/v) per cultural medium.

Any temperature at which microorganism strains to be used can suitably be propagated may be selected as a culture temperature, and an appropriate temperature is usually in the range of from about 15 to 37° C., more preferably from about 20 to 30° C.

Any culture method such as liquid culture and solid culture may be used for the culture as long as it allows propagation of microorganism and production of PHA. In addition, any type of culture method such as batch culture, fed-batch culture, semi-continuous culture and continuous culture may be used. Forms of liquid batch culture include a method of supplying oxygen while shaking the microorganism in a shake flask, and a method of supplying oxygen adopting a stirring ventilation system with a jar fermenter.

For the method of making the microorganism produce and accumulate PHA, a two-step culture method in which the microorganism is cultured by two steps may be adopted other than the one-step culture method in which the microorganism is cultured in an inorganic salt culture medium containing a phosphate and a nitrogen source such as an ammonium salt or a nitrate with a matrix added therein in a predetermined concentration as described above. In this two-step culture method, the microorganism is once propagated sufficiently in the inorganic salt culture medium containing a phosphate and a nitrogen source such as an ammonium salt or a nitrate with a matrix added therein in a predetermined concentration as a primary culture, and thereafter cells obtained by the primary culture are relocated to a culture medium with a matrix added therein in a predetermined concentration after limiting the amount of nitrogen source such as ammonium chloride contained in the culture medium, and are further cultured as a secondary culture, thereby making the microorganism produce and accumulate PHA. Use of this two-step culture method may improve the productivity of desired PHA.

Generally, a produced PHA type polyester has reduced water solubility because of the presence of hydrophobic atom groups such as a bromoalkyl group derived from a 3-hydroxy-ω-bromoalakanoic acid unit in the side chain, and is accumulated in cells of the microorganism capable of producing PHA, and therefore can easily be separated from the culture medium by collecting cells propagated by culture and involved in production and accumulation the desired PHA type polyester. After the collected cells are washed and dried, the desired PHA type polyester can be collected.

In addition, PHA is usually accumulated in cells of such a microorganism capable of producing PHA. For the method of collecting desired PHA from these microorganism cells, a method that is usually used may be adopted. For example, extraction with organic solvents such as chloroform, dichloromethane and acetone is most convenient. Other than the above described solvents, dioxane, tetrahydrofuran and acetonitrile may be used. In addition, in a working environment in which use of any organic solvent is not preferred, a method in which in stead of solvent extraction, any one of a treatment by surfactants such as SDS, a treatment by enzymes such as lysozyme, a treatment by chemicals such as hypochlorites, ammonium and EDTA, an ultrasonic crashing method, a homogenizer method, a pressure crushing method, a bead impulse method, a grinding method, an immersion method and a freeze-thaw method is used to physically crush microorganism cells, followed by removing cell components other than PHA to collect PHA may be adopted.

As one example of inorganic salt culture media capable of being used in the production method of the present invention, the composition of the inorganic salt culture medium (M9 culture medium) used in Examples described later is shown below.
Composition of M9 Culture Medium:
Na$_2$HPO$_4$: 6.3
KH$_2$PO$_4$: 3.0
NH$_4$Cl: 1.0
NaCl: 0.5
(by g/L, at pH=7.0).

Further, for ensuring satisfactory propagation of cells and associated improvement of productivity of PHA, an essential trace element such an essential trace metal element should be added in an appropriate amount to an inorganic salt culture medium such as the above described M9 culture medium, and it is very effective to add about 0.3% (v/v) trace component solution of which composition is shown below. The addition of such a trace component solution supplies a trace metal element for use in propagation of the microorganism.
Composition of Trace Component Solution
nitrilotriacetic acid: 1.5;
MgSO$_4$: 3.0; MnSO$_4$: 0.5; NaCl: 1.0;
FeSO$_4$: 0.1; CaCl$_2$: 0.1; CoCl$_4$: 0.1;
ZnSO$_4$: 0.1; CuSO$_4$: 0.1; AlK(SO$_4$)$_2$: 0.1;
H$_2$BO$_3$: 0.1; Na$_2$MoO$_4$: 0.1; NiCl$_2$: 0.1
(g/L).

A matrix for producing desired PHA, namely at least one type of ω-substituted alkanoic acid compound expressed by chemical formula (22) or at least one type of ω-cyclohexylalkanoic acid compound expressed by chemical formula (23) in addition to ω-bromoalkanoic acids each expressed by chemical formula (21) are made to coexist in the culture, whereby PHA containing 3-hydroxy-ω-substituted alkanoic acid units each expressed by chemical formula (5) or 3-hydroxy-ω-cyclohexylalkanoic acid units from chemical formula (6) besides 3-hydroxy-ω-bromoalkanoic acid units from chemical formula (21) can be produced. The contents of ω-bromoalkanoic acid expressed by chemical formula (21), ω-substituted alkanoic acid compound expressed by chemical formula (22) and ω-cyclohexylalkanoic acid compound expressed by chemical formula (23) are selected so that they are in the range of from 0.0005 to 1% (w/v), more preferably from 0.001 to 0.2% (w/v) per culture medium, respectively.

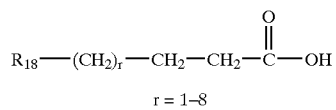

(22)

r = 1–8

(r is an integer number selected from 1 to 8; R$_{18}$ includes a residue having any one of a phenyl structure and a thienyl structure, and represents any one selected from the group consisting of formulas (7), (8), (9), (10), (11), (12), (13), (14), (15), (16) and (17), and in the case where a plurality of types of compounds exists, R$_{18}$ and r in one unit can be different from them in another respectively.

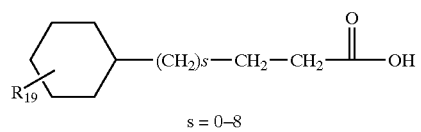

(23)

s = 0–8

(In the formula, R$_{19}$ represents a substituent group in the cyclohexyl group, and R$_{19}$ is selected from the group consisting of H, CN, NO$_2$, a halogen atom, CH$_3$, C$_2$H$_5$, C$_3$H$_7$, CF$_3$, C$_2$F$_5$ and C$_3$F$_7$, s is an integer number selected from 0 to 8.)

(Method of Producing Polyhydroxyalkanoate Expressed by Chemical Formula (1))

The reaction between the polyhydroxyalkanoate having units each expressed by the chemical formula (18) in the present invention and the compound expressed by chemical formula (19) will be described in detail.

The compound expressed by chemical formula (19) for use in the present invention is used in the amount in the range of from 0.1 to 50.0 times in mole, more preferably from 1.0 to 30.0 times in mole as large as the amount of unit expressed by chemical formula (18) to be used as a starting material.

The reaction in the present invention is preferably made to proceed under a basic condition. For the base, amines such as dimethyl amine, diethyl amine, trimethyl amine, triethyl amine, dibutyl amine, morpholine and piperidine, alkali hydroxide metals such as sodium hydrate and potassium hydrate, alkali carbonate metals such as sodium carbonate and potassium carbonate, alkali metal alcoholates such as sodium methylate and sodium ethylate, sodium hydride and the like may be used. Particularly, diethyl amine, triethyl amine and dibutyl amine are preferably used. The amount of base to be used is in the range of from 0.1 to 100.0 times in mole, more preferably from 0.5 to 50.0 times in mole as large as the amount of unit expressed by chemical formula (18).

A solvent may be used as required in the reaction of the present invention. Solvents to be used include hydrocarbons such as hexane, cyclohexane and heptane, ketones such as acetone, methyl ethyl ketone, ethers such as dimethyl ether, diethyl ether, tetrahydrofuran, halogenated hydrocarbons such as dichloromethane, chloroform, carbon tetrachloride, dichloroethane, and trichloroethane, aromatic hydrocarbons such as benzene and toluene, and aprotic polar solvents such as N,N-dimethyl formamide and dimethyl sulfoxide. N,N-dimethyl formamide is particularly preferably used. The amount of solvent to be used may be determined as appropriate according to the type of starting material, the type of base, the reaction condition and the like.

In the method of the present invention, the reaction temperature is not particularly limited, but is usually in the range of from 0° C. to the boiling point of the solvent. In the case where the reaction temperature is higher than a room temperature, however, the ester linkage of the main chain may be cut, and it is therefore more preferable that the reaction is made to proceed at a temperature of about 0 to 30° C.

In the method of the present invention, the reaction time cannot be determined unconditionally, but is usually in the range of from 1 to 48 hours.

In the present invention, the reaction solution containing the polyhydroxyalkanoate of chemical formula (1) produced in this way can be removed using distillation as a normal method. Alternatively, the reaction solution can be collected by mixing the reaction solution uniformly with a solvent insoluble in the polyhydroxyalkanoate expressed by chemical formula (1) to reprecipitate the desired polyhydroxyalkanoate expressed by chemical formula (1) using a solvent such as water, an alcohol such as methanol and ethanol, and an ether such as dimethyl ether, diethyl ether and tetrahydrofuran. The polyhydroxyalkanoate of chemical formula (1) obtained in this way may be isolated and purified if necessary. The isolation and purification method is not particularly limited, and a method in which a solvent insoluble in the polyhydroxyalkanoate expressed by chemical formula (1) is used to reprecipitate the polyhydroxyalkanoate, a method using column chromatography and a method using dialysis may be used.

Furthermore, in the reaction in the present invention, the reaction solvent, the reaction temperature, the reaction time and the purification method should not be limited to those described above.

In addition, the present invention is a charge controlling agent containing the above described polyhydroxyalkanoate, and further an electrostatic latent image developing toner containing the charge controlling agent. The present invention is further an image formation method comprising an charging step of applying a voltage to a charge member from the outside to uniformly charge an electrostatic latent image carrier for the above electrostatic latent image developing toner, a development step of forming a toner image on the electrostatic latent image carrier, a transfer step of transferring the toner image on the electrostatic latent image carrier to a transfer material via or not via an intermediate transfer body, and a heat-fixation step of fixing by heat the toner image on the transfer material, and also an image forming apparatus comprising means corresponding to respective steps of the method, namely charging means, development means, transfer means and heat-fixation means.

The polyhydroxyalkanoate for use in the present invention has good compatibility with the binder resin and excellent compatibility particularly with polyester type binder resin. Since the toner containing the polyhydroxyalkanoate of the present invention has a high specific charge level and is excellent in stability with time, it provides clear images with stability in image formation with electrostatic recording even after being stored for a long time period, and the toner can be produced for both negatively charged black toners and color toners because of its colorlessness and negative-electrifiability.

In addition, by properly selecting the type and composition ratio of monomer units constituting the polyhydroxyalkanoate of the present invention, wide range compatibility control is made possible. If a resin composition in which the charge controlling agent is put in micro-phase separation state in a toner binder, no electric continuity is formed in the toner so that electric charge can stably be maintained. In addition, the polyhydroxyalkanoate of the present invention contains no heavy metals, and therefore when the toner is produced by suspension polymerization or emulsion polymerization, polymerization inhibition caused due to the presence of heavy metals, as found in the case of a metal-containing charge controlling agent, does not occur, thus making it possible to produce a toner with stability.

(Addition of PHA to Toner)

In the present invention, the method for adding the above compound to a toner may be a method of internal addition to the toner and a method of external addition to the toner. The addition amount of the internal addition is generally 0.1 to 50% by weight, preferably 0.3 to 30% by weight, and further preferably 0.5 to 20% by weight as the weight ratio of the toner binder and the charge controlling agent. If it is lower than 0.1% by weight, the improvement degree of the charging property of the toner is insignificant and thus not preferable. Whereas, if it is higher than 50% by weight, it is not preferably from an economical point of view. Further, in the case of the external addition, the weight ratio of the toner binder and the charge controlling agent is preferably 0.01 to 5% by weight, and it is particularly preferable that the compound is mechanochmically fixed on the surface of the toner. In addition, the compound presented in the present invention may be used in combination of a known charge controlling agent.

The number-average molecular weight of the above-described compound of the present invention is usually 1000 to 1000000, preferably 1000 to 500000. If it is less than 1000, the compound is completely compatible with the toner binder to make it difficult to form a discontinuous domain, resulting in an insufficient charge level, and the fluidity of the toner is adversely affected. Further, if it is higher than 1000000, dispersion in the toner becomes difficult.

The molecular weight of PHA of the present invention can be measured as a relative or absolute molecular weight. It can conveniently be measured by, for example, GPC (gel permeation chromatography). For the specific measurement process of GPC, PHA is dissolved in a solvent capable of dissolving the PHA in advance, and a measurement is made with a similar mobile phase. For the detector, a differential refraction detector (RI), an ultraviolet detector (UV) or the like may be used depending on the PHA to be measured. The molecular weight is determined as a relative comparison with a standard sample (polystyrene, polymethylmethacrylate, etc.). The solvent may be selected from solvents capable of dissolving a polymer such as dimethylformamide (DMF), dimethylsulfoxide (DMSO), chloroform, tetrahydrofuran (THF), toluene, hexafluoroisopropanol (HFIP). In the case of a polar solvent, a measurement can be made by addition of salt. In addition, in the present invention, compounds presented in the present invention with the ratio (Mw/Mn) of the weight average molecular weight (Mw) to the number-average molecular weight (Mn) measured as described above being in the range of from 1 to 10 are preferably used.

In the present invention, the compound presented in the present invention has a melting point preferably in the range of from 20 to 150° C., especially preferably from 40 to 150° C., or has no melting point but a glass transition temperature in the range of from 20 to 150° C., especially preferably from 40 to 150° C. If the foregoing melting point is lower than 20° C. or the glass transition temperature with no melting point is lower than 20° C., the fluidity and the storage property of the toner are often adversely affected. Whereas if the foregoing melting point is higher than 150° C. or the glass transition temperature with no melting point is higher than 150° C., the charge controlling agent becomes difficult to be kneaded with the toner and the charge level distribution becomes broad in many cases.

To measure the melting point Tm and the glass transition temperature Tg in this case, a high precision and internally heating input compensation type differential scanning calorimeter, for example, DSC-7 manufactured by Perkin Elmer Co., may be employed.

Regarding the toner binder and the electrostatic latent image developing toner of the present invention, the weight ratio of the toner binder and the charge controlling agent is generally 0.1 to 50% by weight, preferably 0.3 to 30% by weight, and more preferably 0.5 to 20% by weight. Regarding the composition ratio of the electrostatic latent image developing toner of the present invention, generally the foregoing charge controlling agent is in the range of from 0.1 to 50% by weight, the toner binder is in the range of from 20 to 95% by weight, and a coloring material is in the range of from 0 to 15% by weight with respect to the weight of the toner and based on the necessity, a magnetic powder (a powder of a ferromagnetic metal such as iron, cobalt, nickel and the like and a compound such as magnetite, hematite, ferrite and the like) functioning as a coloring material may be added in an amount not more than 60% by weight. Further, various additives [a lubricant (polytetrafluoroethylene, a lower molecular weight polyolefin, an aliphatic acid or its metal salt or amide, and the like) and other charge controlling agents (metal-containing azo dye, metal salcylate, etc.)] may be contained. In addition, in order to improve the fluidity of the toner, a hydrophobic colloidal silica fine powder may also be employed. The amounts of these additives are generally not more than 10% by weight on the bases of the toner weight.

In the toner of the present invention, it is preferable for at least some of the toner binder to form a continuous phase and at least some of the charge controlling agent to form discontinuous domain. As compared with the case where the charge controlling agent has complete compatibility with the toner binder without forming the discontinuous domain, the added charge controlling agent is easily exposed to the surface and effective even in a small amount. The dispersion particle diameter of the domain is preferably 0.01 to 4 $\mu$m and more preferably 0.05 to 2 $\mu$m. If it is bigger than 4 $\mu$m, the dispersibility becomes insufficient and the charge level distribution becomes broad and the transparency of the toner is deteriorated. Whereas, if the dispersion particle diameter is smaller than 0.01 $\mu$m, it becomes similar to the case where the charge controlling agent has complete compatibility with the binder without forming discontinuous domain, a large amount of the charge controlling agent is required to be added. That at least some of the foregoing charge controlling agent forms the discontinuous domain and the dispersion particle size can be observed by observing a specimen of the toner with a transmission electron microscope. In order clearly observe the interface, it is also effective to carry out observation of a toner specimen by electron microscope after the specimen is dyed with ruthenium tetraoxide, osmium tetraoxide and the like.

Further, for the purpose of reducing the particle diameter of the discontinuous domain formed by the compound presented in the present invention, a polymer compatible with the compound presented in the present invention and also with the toner binder may be added as a compatible agent. The compatibility enhancing agent is, among other things, a polymer comprising mutually graft- or block-polymerized polymer chains containing at least 50% by mol of monomers having practically similar structure to that of the constituent monomers of the compound presented in the present invention and polymer chains containing at least 50% by mol of monomers having practically similar structure to that of the toner binder. The amount of the compatible agent to be used is generally not more than 30% by weight and preferably 1 to 10% by weight, with respect to the compound presented in the present invention.

(Other Constituent Materials)

Other constituent materials constituting the electrostatic latent image developing toner of the present invention will be described below.

(Binder Resin)

At first, any resin may be used as the binder resin without any particular restrictions if it is generally used for production of a toner. Also, the charge controlling agent of the present invention may previously be mixed with the binder resin to be used as a toner binder composition of the present invention having charge controlling capability before production of the toner. For example, styrene-based polymers, polyester-based polymers, epoxy-based polymers, polyolefin-based polymers, polyurethane-based polymers and the like can exemplify the binder resin, and they are used alone or while being mixed with one another.

The styrene-based polymers may be styrene(meth)acrylic acid ester copolymers and copolymers of these copolymers with other monomers copolymerizable with them; copolymers of styrene with diene type monomers (butadiene, isoprene and the like) and copolymers of these copolymers with other monomers copolymerizable with them; and the like. The polyester-based polymers may be condensation polymerization products of aromatic dicarboxylic acid and aromatic diol alkylene oxide addition products and the like. The epoxy-based polymers may be reaction products of aromatic diols and epichlorohydrin and their modified products. The polyolefin-based polymers may be polyethylene, polypropylene, and copolymer chains of these polymers with monomers polymerizable with them. The polyurethane-based polymers may be addition polymerization products of aromatic diisocyanates and aromatic diol alkylene oxide addition products and the like.

Practical examples of the binder resin to be employed in the present invention are polymers of the following polymerizable monomers or their mixtures, or copolymerization products produced from two or more kinds of the following polymerizable monomers. Such polymers are more particularly, for example, styrene-based polymers such as styrene-acrylic acid copolymer, styrene-methacrylic acid copolymer and the like; polyester-based polymers; epoxy-based polymers; polyolefin-based polymers; and polyurethane-based polymers and they are preferably used.

Practical examples of the polymerizable monomers are styrene and its derivatives such as styrene, o-methylstyrene, m-methylstyrene, p-methylstyrene, p-methoxystyrene, p-phenylstyrene, p-chlorostyrene, 3,4-dichlorostyrene, p-ethylstyrene, 2,4-dimethylstyrene, p-n-butylstyrene, p-tert-butylstyrene, p-n-hexylstyrene, p-n-octylstyrene, p-n-nonylstyrene, p-n-decylstyrene, p-n-dodecylstyrene, and the like; ethylenic unsaturated monoolefins such as ethylene, propylene, butylene, isobutylene and the like; unsaturated polyenes such as butadiene and the like; vinyl halides such as vinyl chloride, vinylidene chloride, vinyl bromide, vinyl fluoride and the like; vinyl esters such as vinyl acetate, vinyl propionate, vinyl benzoate and the like; $\alpha$-methylene aliphatic monocarboxylic acid esters such as methyl methacrylate, ethyl methacrylate, propyl methacrylate, n-butyl methacrylate, isobutyl methacrylate, n-octyl methacrylate, dodecyl methacrylate, 2-ethylhexyl methacrylate, stearyl methacrylate, phenyl methacrylate, dimethylaminoethyl methacrylate, diethylaminoethyl methacrylate, and the like; acrylic acid esters such as methyl acrylate, ethyl acrylate, n-butyl acrylate, isobutyl acrylate, propyl acrylate, n-octyl acrylate, dodecyl acrylate, 2-ethylhexyl acrylate, stearyl acrylate, 2-chloroethyl acrylate, phenyl acrylate, and the like; vinyl ethers such as vinyl methyl ether, vinyl ethyl ether, vinyl isobutyl ether, and the like; vinyl ketones such as vinyl methyl ketone, vinyl hexyl ketone, vinyl isopropenyl ketone, and the like; N-vinyl compounds such as N-vinylpyrrole, N-vinylcarbazole, N-vinylindole, N-vinylpyrrolidone and the like; vinyl naphthalenes; acrylic acid or methacrylic acid derivatives such as acrylonitrile, methacrylonitrile, acrylamide and the like; esters of the above-described $\alpha,\beta$-unsaturated acid; diesters of bibasic acid; dicarboxylic acids such as maleic acid, methyl maleate, butyl maleate, dimethyl maleate, phthalic acid, succinic acid, terephthalic acid, and the like; polyols compounds such as ethylene glycol, diethylene glycol, triethylene glycol, 1,2-propylene glycol, 1,3-propylene glycol, 1,4-butanediol, 1,6-hexanediol, bisphenol A, hydrogenated bisphenol A, polyoxyethylene-modified bisphenol A and the like; isocyanates such as p-phenylene diisocyanate, p-xylylene diisocyanate, 1,4-tetramethylene diisocyanate, and the like; amines such as ethylamine, butylamine, ethylenediamine, 1,4-diaminobenzene, 1,4-diaminobutane, monoethanolamine, and the like; epoxy compounds such as diglycidyl ether, ethylene glycol diglycidyl ether, bisphenol A glycidyl ether, hydroquinone glycidyl ether, and the like.

(Cross-Linking Agent)

In the case of producing the binder resin to be employed in the present invention, based on the necessity, the following cross-linking agent may be used. Examples of a bifunctional cross-linking agent are divinylbenzene, bis(4-acryloxypolyethoxyphenyl)propane, ethylene glycol diacrylate, 1,3-butylene glycol diacrylate, 1,4-butanediol diacrylate, 1,5-pentanediol diacrylate, 1,6-hexanediol diacrylate, neopentyl glycol diacrylate, diethylene glycol diacrylate, triethylene glycol diacrylate, tetraethylene glycol diacrylate, respective diacrylates of polyethylene glycol #200, #400, #600, dipropylene glycol diacrylate, polypropylene glycol diacrylate, polyester type diacrylate, and those obtained by changing these exemplifying acrylates into corresponding methacrylates.

Examples of bi- or higher polyfunctional cross-linking agent are pentaerythritol triacrylate, trimethylolethane triacrylate, trimethylolpropane triacrylate, tetramethylolmethane tetraacrylate, oligoester acrylates or methacrylates, 2,2-bis(4-methacryloxy polyethoxyphenyl)propane, diallyl phthalate, triallyl cyanurate, triallyl azocyanurate, triallyl isocyanurate, triallyl trimellitate, diaryl chlorendate, and the like.

Polymerization Initiator

In the case of producing the binder resin to be employed for the present invention, the following polymerization initiators may be used based on the necessity: for example, tert-butyl peroxy-2-ethylhexanoate, cumine perpivalate, tert-butyl peroxylaurate, benzoyl peroxide, lauroyl peroxide, octanoyl peroxide, di-tert-butyl peroxide, tert-butylcumyl peroxide, dicumyl peroxide, 2,2'-azobis isobutyronitrile, 2,2'-azobis(2-methylbutyronitrile), 2,2'-azobis(2,4-dimethylvaleronitrile), 2,2'-azobis(4-methoxy-2,4-dimethylvaleronitrile), 1,1-bis(tert-butylperoxy)-3,3,5-trimethylcyclohexane, 1,1-bis(tert-butylperoxy) cyclohexane, 1,4-bis(tert-butylperoxycarbonyl) cyclohexane, 2,2-bis(tert-butylperoxy)octane, n-butyl 4,4-bis(tert-butylperoxy)valerate, 2,2-bis(tert-butylperoxy) butane, 1,3-bis(tert-butylperoxyisopropyl)benzene, 2,5-dimethyl-2,5-di(tert-butylperoxy)hexane, 2,5-dimethyl-2,5-di(benzoylperoxy)hexane, di-tert-butyldiperoxy isophthalate, 2,2-bis(4,4-di-tert-butylperoxycyclohexyl) propane, di-tert-butylperoxy-$\alpha$-methylsuccinate, di-tert-butyl peroxydimethylglutarate, di-tert-butyl peroxyhexahydroterephthalate, di-tert-butyl peroxyazelate, 2,5-dimethyl-2,5-di(tert-butylperoxy)hexane, diethylene glycol bis(tert-butylperoxycarbonate), di-tert-butyl peroxytrimethyladipate, tris(tert-butylperoxy)triazine, vinyltris(tert-butylperoxy)silane and the like. Each of these compounds may be used alone or in combination. The use amount of them is generally in 0.05 parts by weight or more (preferably 0.1 to 15 parts by weight) to 100 parts by weight of monomers.

(Other Biodegradable Plastics)

In addition, in the present invention, biodegradable plastics are preferably used. Examples of the biodegradable plastics are "Ecostar", "Ecostar plus" (produced by Hagiwara Industries, Inc.), "Biopole" (produced by Monsant Co.), "Ajicoat" (Ajinomoto Co., Ltd.), "Placcel", "Polycaprolactone" (produced by Daicel Chem., Ind., Ltd.), "Bionolle" (produced by Showa Highpolymer Co., LTD), "Lacty" (produced by Shimadzu Corporation), "Lacea" (produced by Mitsui Chemicals, Inc.) and the like.

It is preferable for the combinations of the binder resin and the charge controlling agent of the present invention that the structure of the polymers of the binder resin and the polymer structure of the polymer chain of the charge controlling agent are similar to each other as much as possible. If the structure of the polymers of the binder resin and the polymer structure of the polymer chain of the charge controlling agent are considerably dissimilar to each other, the charge controlling agent tends to be dispersed insufficiently in the binder resin.

The weight ratio of the charge controlling agent of the present invention to be internally added to the binder resin is generally 0.1 to 50% by weight, preferably 0.3 to 30% by weight, and more preferably 0.5 to 20% by weight. If the weight ratio of the charge controlling agent to be internally added is lower than 0.1% by weight, the charge level becomes low and if the weight ratio is higher than 50% by weight, the charge stability of the toner is deteriorated.

(Coloring Agent)

Any coloring agent generally used for production of a toner may be used as the coloring agent composing the electrostatic latent image developing toner of the present invention without particular restrictions. For example, carbon black, titanium white, and any other pigment and/or dye may be used. For example, in the case the electrostatic latent image developing toner of the present invention is used for a magnetic color toner, examples of the coloring agent to be employed are C.I. Direct Red 1, C.I. Direct Red 4, C.I. Acid Red 1, C.I. Basic Red 1, C.I. Mordant Red 30, C.I. Direct Blue 1, C.I. Direct Blue 2, C.I. Acid Blue 9, C.I. Acid Blue 15, C.I. Basic Blue 3, C.I. Basic Blue 5, C.I. Mordant Blue 7, C.I. Direct Green 6, C.I. Basic Green 4, C.I. Basic Green 6 and the like. Examples of the pigment are Chrome Yellow, Cadmium Yellow, Mineral Fast Yellow, Navel Yellow, Naphthol Yellow S, Hansa Yellow G, Permanent Yellow NCG, Tartrazine Yellow Lake, Chrome Orange, Molybdenum Orange, Permanent Orange GTR, Pyrazolone Orange, Benzidine Orange G, Cadmium Red, Permanent Red 4R, Watching Red calcium salt, Eosine Lake, Brilliant Carmine 3B, Manganese Violet, Fast Violet B, Methyl Violet Lake, Prussian Blue, Cobalt Blue, Alkali Blue Lake, Victoria Blue Lake, Phthalocyanine Blue, Fast Sky Blue, Indanthrene Blue BC, Chrome Green, chromium oxide, Pigment Green B, Malachite Green Lake, Final Yellow Green G and the like.

In the case the electrostatic latent image developing toner of the present invention is used for a two-component type full color toner, the following coloring agents can be used. For example, coloring pigments for magenta toners are C.I. Pigment Red 1, 2, 3, 4, 5, 6, 7, 8, 9, 10, 11, 12, 13, 14, 15, 16, 17, 18, 19, 21, 22, 23, 30, 31, 32, 37, 38, 39, 40, 41, 48, 49, 50, 51, 52, 53, 54, 55, 57, 58, 60, 63, 64, 68, 81, 83, 87, 88, 89, 90, 112, 114, 122, 123, 163, 202, 206, 207, 209, C.I. Pigment Violet 19, C.I. Vat Red 1, 2, 10, 13, 15, 23, 29, 35 and the like.

In the present invention, the above-exemplified pigments may be used alone, but it is more preferable that they are used in combination with dyes for improving the clearness from the aspect of the full color image quality. In such a case, the examples of usable magenta dyes are oil-soluble dyes such as C.I. Solvent Red 1, 3, 8, 23, 24, 25, 27, 30, 49, 81, 82, 83, 84, 100, 109, 121, C.I. Disperse Red 9, C.I. Solvent Violet 8, 13, 14, 21, 27, and C.I. Disperse Violet 1 and the like; and basic dyes such as C.I. Basic Red 1, 2, 9, 12, 13, 14, 15, 17, 18, 22, 23, 24, 27, 29, 32, 34, 35, 36, 37, 38, 39, 40, C.I. Basic Violet 1, 3, 7, 10, 14, 15, 21, 25, 26, 27, 28, and the like.

As other coloring pigments, examples of cyan coloring pigments are C.I. Pigment Blue 2, 3, 15, 16, 17, C.I. Vat Blue 6, C.I. Acid Blue 45, copper-phthalocyanine pigments having a phthalocyanine skeleton containing substituents of phthalimidomethyl groups in number of 1 to 5, and the like.

Examples of yellow coloring pigments are C.I. Pigment Yellow 1, 2, 3, 4, 5, 6, 7, 10, 11, 12, 13, 14, 15, 16, 17, 23, 65, 73, 83, C.I. Vat Yellow 1, 3, 20 and the like.

The above-described dyes and pigments may be used solely or may be used while being optionally mixed with one another to obtain desired hue of the toner. Incidentally, taking the environmental preservation and the safety to human being into consideration, a variety of edible coloring elements may preferably be used. The content of the coloring agents in the toner may widely altered depending on the desired coloration effects. Generally, in order to obtain the best toner properties, that is, in consideration of the printing coloration capability, the toner shape stability, and the toner leap, these coloring agents are used at a ratio in the range of from 0.1 to 60 parts by weight, preferably 0.5 to 20 parts by weight with respect to 100 parts by weight of the binder resin.

Other Components of Toner

In the electrostatic latent image developing toner of the present invention may contain the following compounds other than the foregoing binder resin and the coloring agent components, to an extent (within a ratio less than the content of the binder resin) in which no undesired effect is caused in the present invention. Examples of such compounds include silicone resin; polyester; polyurethane; polyamide; epoxy resin; poly(vinyl butyral); rosin; modified rosin; terpene resin; phenolic resin; aliphatic or alicyclic hydrocarbon resin such as lower molecular weight polyethylene and lower molecular weight polypropylene; aromatic type petroleum resin; and chlorinated paraffin and paraffin waxes. Among them, preferable waxes to be used are practically lower molecular weight polypropylene and its byproducts, lower molecular weight polyester, and ester type wax and aliphatic derivatives. Among these waxes, waxes separated based on the molecular weight of the waxes by various methods are also preferably used in the present invention. Further, after separation, the waxes may be modified to control the acid values, block-copolymerized, or graft-modified.

Specially, in the electrostatic latent image developing toner of the present invention, in the case such wax components as described above are added and these wax components are found practically dispersed in the binder resin in spherical and/or elliptical island state by cross-sectional observation of the toner by a transmission electron microscope, the toner is provided with excellent properties.

Method of Producing Toners

Any conventionally known method may be employed for a practical method for producing an electrostatic latent image developing toner of the present invention having the constitution as described above. The electrostatic latent image developing toner of the present invention can be produced, for example, by a so-called pulverization method for obtaining a toner through the following steps. Specifically, the compound presented in the present invention described previously, resin materials such as binder resin, and a wax to be added as necessary are sufficiently mixed by a mixer such as a Henshel mixer, a ball mill and the like and then melted and kneaded using a thermally kneading apparatus such as heating rolls, a kneader, an extruder and the like to make the resin material compatible with one another, and as coloring agents, pigments, dyes, or magnetic materials and also additives such as metal compounds to be added as necessary are dispersed or dissolved in the resulting mixture, and after solidification of the mixture by cooling, the obtained solidified product is pulverized by a pulverizing apparatus such as a jet mill, a ball mill and the like and then classified to obtain an electrostatic latent image developing toner of the present invention with a desired particle size. In the above-described classification step, from an aspect of productivity, a multi-step classification apparatus is preferably used.

In addition, the electrostatic latent image developing toner of the present invention with a desired particle size can be obtained by mixing and stirring the binder resin and the compound of the present invention in a solvent (e.g., aromatic hydrocarbons such as toluene, xylene and the like; halogen compounds such as chloroform, ethylene dichloride, and the like; ketones such as acetone, methyl ethyl ketone, and the like; amides such as dimethylformamide and the like), and then adding the resulting mixture to water to re-precipitate the solid, then filtering and drying the solid, and further pulverizing it by a pulverizing apparatus such as a jet mill, a ball mill and the like, and finally classifying the pulverized matter. In the above-described classification step, from an aspect of productivity, a multi-step classification apparatus is preferably used.

In addition, the electrostatic latent image developing toner of the present invention can be produced by a so-called polymerization method as follows. That is, in this case, the compound of the present invention, a polymerizable monomer, and as coloring agents, pigments, dyes, or magnetic materials and also based on the necessity, additives such as a cross-linking agent, a polymerization initiator, waxes, and others are mixed and dispersed and in the presence of a surfactant or the like, the mixture is subjected to suspension polymerization to obtain a polymerizable and coloring resin particle, and after the obtained particle is separated by solid-liquid separation, the particle is dried and classified if necessary to obtain an electrostatic latent image developing toner of the present invention with a desired particle size.

Furthermore, a coloring fine particle containing no charge controlling agent is produced by the above-described manner and then either solely or together with an externally added agent such as colloidal silica, the compound presented in the present invention may be stuck and added to the surface of the particle by a mechanochemical method or the like.

(Externally Added Silica Agent)

In the present invention, a silica fine powder is preferably added externally to the toner produced in a manner as described above for improving the charge stability, development characteristic, fluidity and durability. The silica fine powder to be employed in this case can provide desirable effects if it has a specific surface area equal to or larger than 20 $m^2/g$ or higher (especially 30 to 400 $m^2/g$) measured based on the nitrogen adsorption by BET method. The content of the silica fine powder to be added is preferably 0.01 to 8 parts by weight, more preferably 0.1 to 5 parts by weight, with respect to 100 parts by weight of the toner particle. In this case, based on the necessity, the silica fine powder to be used in the case is preferably treated for the purpose of controlling the hydrophobicity and charging property with silicone varnish, variously modified silicone varnish, silicone oil, variously modified silicone oil, a silane coupling agent, a silane coupling agent having a functional group, and other organosilicon compounds. These treatment agent may be used by mixing.

Inorganic Powder

Further, in order to improve the development capability and the durability, the following inorganic powder is preferably added. Examples of the powder are oxides of metals such as magnesium, zinc, aluminum, cerium, cobalt, iron, zirconium, chromium, manganese, strontium, tin, antimony and the like; compounded metal oxides such as calcium titanate, magnesium titanate, and strontium titanate; metal salts such as calcium carbonate, magnesium carbonate and aluminum carbonates; clay minerals such as kaolin; phosphate compounds such as apatite; silicon compounds such as silicon carbide, and silicon nitride; and carbon powder such as carbon black and graphite. Among them, fine powders of zinc oxide, aluminum oxide, cobalt oxide, manganese dioxide, strontium titanate, and magnesium titanate are preferably used.

Lubricant

Further, the following lubricant powder may be added to the toner. For example, fluoro resin such as Teflon, poly (vinylidene fluoride) and the like; fluoride compounds such as carbon fluoride; aliphatic acid metal salts such as zinc stearate; aliphatic acid derivatives such as aliphatic acid, aliphatic acid esters and the like; and molybdenum sulfide.

(Carrier)

The electrostatic latent image developing toner of the present invention having the above-described constitution is usable for a variety of conventionally known toners; solely as a non-magnetic mono-component developer, as a non-magnetic toner together with a magnetic carrier for composing a magnetic two-component developer, as a magnetic toner to be used solely for a magnetic mono-component toner. In this case, as the carrier to be used in the case of the two-component development, any conventionally known carrier may be used. More particularly, particles of surface-oxidized or non-oxidized metals such as iron, nickel, cobalt, manganese, chromium and rare earth metals, their alloys and oxides and having an average particle size of 20 to 300 $\mu$m may be used as the carrier particle. Further, the carrier to be used in the present invention are preferably the above-described carrier particle whose surface bears or is coated with a substance such as styrene-based resin, acrylic resin, silicone resin, fluoro resin, polyester resin and the like.

(Magnetic Toner)

The electrostatic latent image developing toner of the present invention may be a magnetic toner by adding a magnetic material to the toner particle. In this case, the magnetic material may take a role also as a coloring agent. The magnetic material to be used in this case may be iron oxides such as magnetite, hematite and ferrite; metals such as iron, cobalt and nickel; alloys of these metals with metals such as aluminum, cobalt, copper, lead, magnesium, tin, zinc, antimony, beryllium, bismuth, cadmium, calcium, manganese, selenium, titanium, tungsten and vanadium; and their mixtures. The magnetic material to be used in the present invention has an average particle size preferably 2 $\mu$m or less, more preferably 0.1 to 0.5 $\mu$m. The amount to be added to the toner is preferably 20 to 200 parts by weight to 100 parts by weight of the binder resin and especially preferably 40 to 150 parts by weight to 100 parts by weight of the binder resin.

In addition, in order to give high image quality, it is required to precisely develop very small latent image dots and for this purpose, for example, it is preferable that the weight average particle size of the electrostatic latent image developing toner of the present invention is controlled so that it is in the range of from 4 to 9 $\mu$m. That is, if the toner particle has a weight average particle size smaller than 4 $\mu$m, the transfer efficiency is decreased and a large amount of the transfer residual toner tends to remain on a photoconductor to result in an undesirable cause of uneven and irregular image formation attributed to fogging and transfer failures. Whereas, if the toner particle has a weight average particle size larger than 9 $\mu$m, letters and line images tend to be eliminated.

In the present invention, the average particle size and the particle size distribution of the toner are measured by using Coulter Counter TA-II model or Coulter Multisizer (manufactured by Coulter Co.) or the like to which an interface (manufactured by Nikka Machine Co.) for outputting the distribution by number, the distribution by volume and a PC9801 personal computer (manufactured by NEC) are connected. As an electrolytic solution to be used at that time, an aqueous 1% NaCl solution is prepared using first-grade sodium chloride. As the electrolytic solution, for example, a commercialized ISOTON R-II (produced by Coulter Scientific Japan Co.) may also be usable. A practical measurement method involves steps of adding 0.1 to 5 ml of a surfactant (preferably an alkylbenzenesulfonic acid salt is used) as a dispersant to 100 to 150 ml of the above-described aqueous solution, further adding 2 to 20 mg of a sample to the resulting solution to obtain a specimen to be measured. At the time of measurement, the electrolytic solution in which the specimen to be measured is suspended is treated for dispersion for 1 to 3 minutes by an ultrasonic dispersing apparatus and then the volume and the number of the toner particles of 2 $\mu$m or larger are measured by the foregoing Coulter Counter TA-II model using 100 $\mu$m apertures as apertures and the distribution by volume and the distribution by number are calculated. Then, the weight average particle size (D4) on the bases of the volume calculated from the distribution by volume according to the present invention and the length average particle size (D1) on the bases of the number calculated from the distribution by number are calculated.

(Charge Level)

In addition, the charge level of the electrostatic latent image developing toner of the present invention is preferably in the range of from −10 to −80 $\mu$C/g, more preferably from −15 to −70 $\mu$C/g per unit weight (two-component method) in improving the transfer efficiency in a transfer method using a transfer member with a voltage applied thereto.

Figure 8:
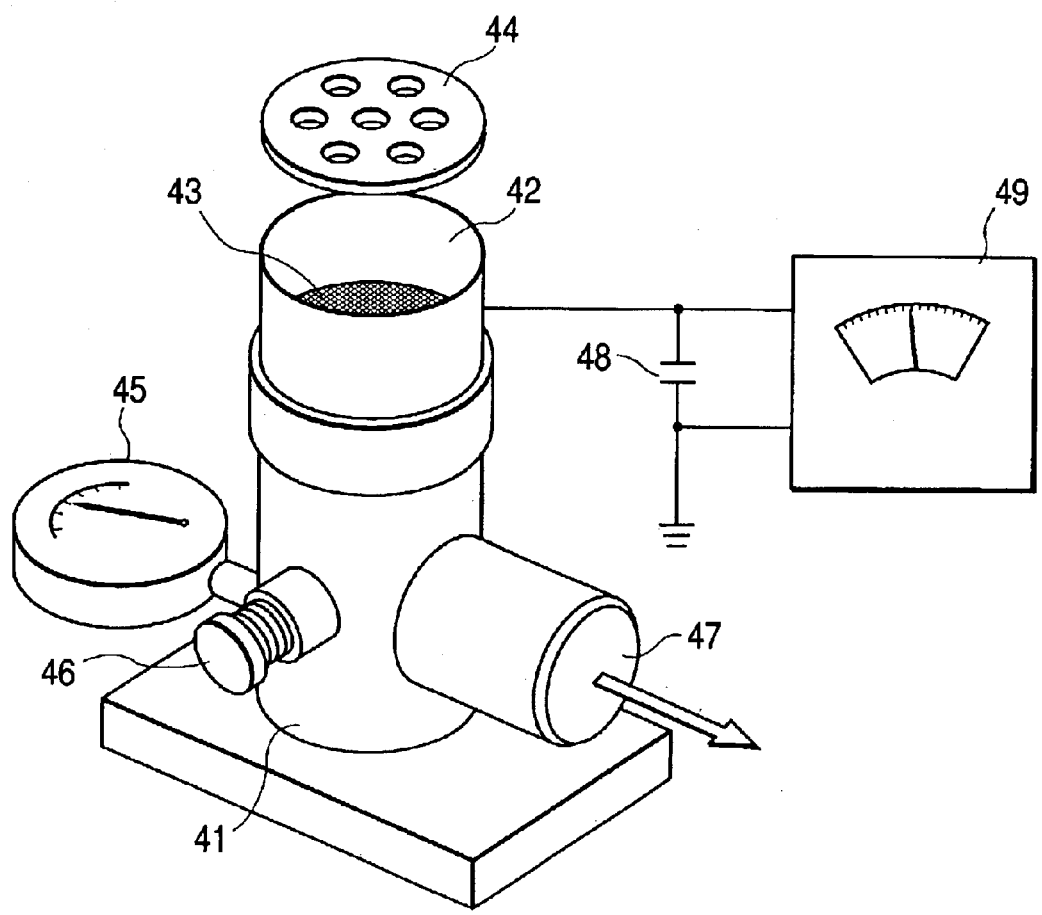
FIG. 8 is a schematic view showing a blow-off charge level measuring apparatus for measuring the charge level of the toner.

The method of measuring an charge level (a two-component tribo) by the two-component method employed in the present invention will be described as follows. A charge level measuring apparatus illustrated in FIG. 8 is used for the measurement. At first, under a specified environment, EFV 200/300 (produced by Powder Tec Co.) is used as a carrier and a bottle made of a polyethylene with a capacity of 50 to 100 ml is charged with a mixture of 9.5 g of the carrier and 0.5 g of a toner, an object to be measured, set in a shaking apparatus so controlled as to keep the amplitude constant, and shaken for a prescribed period in the shaking conditions of an amplitude of 100 mm and a shaking speed of 100 time reciprocation per 1 minute. Then, 1.0 to 1.2 g of the above mixture is placed in a measurement container 42 made of metal having a 500-mesh screen 43, and the measurement container 42 is covered with a metal lid 44 in the bottom of the charge level measuring apparatus shown in FIG. 8. The total weight of the measurement container 42 at that time is measured and determined as W1 (g). Next, the gas in the container is aspirated through a suction port 47 by an unillustrated aspirator (at least the portion contacting the measurement container 42 is made of an insulator) and an air ventilation adjustment valve 46 is controlled to control the pressure of the vacuum meter 45 to be 2,450 Pa (250 mmAq). Under such a state, aspiration is carried out for 1 minute to suck and remove the toner. The potential of a potentiometer 49 at that time is denoted as V (volt). The reference numeral 48 denotes a capacitor and the capacity is denoted as C ($\mu$F). The weight of the entire measurement container after the aspiration is weighed and denoted as W2 (g). The friction charge level ($\mu$C/g) of the toner can be calculated according to the following equation from these measurement values.

$$\text{Friction charge level } (\mu C/g) = C \times V/(W1-W2)$$

(Molecular Weight Distribution of Binder Resin)

The binder resin for use in the constituent material of the electrostatic latent image developing toner of the present invention preferably has a peak within the range of from 3,000 to 15,000 in a low molecular weight region of the molecular weight distribution measured by GPC, especially, in the case of production by the pulverization method. That is, if the GPC peak exceeds 15,000 in the low molecular weight region, it sometimes becomes difficult to obtain a toner with a sufficiently improved transfer efficiency. Whereas if binder resin having a GPC peak of less than 3,000 is used, melting takes place easily at the time of surface treatment and therefore it is undesirable.

In the present invention, the molecular weight of the binder resin is measured by GPC (gel permeation chromatography). A practical GPC measurement method is carried out as follows: a toner previously extracted with THF (tetrahydrofuran) solvent for 20 hours using a Soxhlet extractor is used as a sample for measurement and using columns A-801, 802, 803, 804, 805, 806, and 807 manufactured by Showa Denko K. K. and calibration curves of standardized polystyrene resins, the molecular weight distribution is measured. Further, in the present invention, it is preferable that the binder resin with the ratio (Mw/Mn) of the weight average molecular weight (Mw) to the number-average molecular weight (Mn) measured as described above being in the range of from 2 to 100 is used.

(Glass Transition Temperature of Toner)

Further, the toner of the present invention is preferably adjusted by using a proper material so as to have a glass transition temperature Tg in the range of from 40 to 75° C., more preferably 52 to 70° C., from a viewpoint of fixation and storage stability. In this case, the measurement of the glass transition temperature Tg may be carried out using a high precision and internally heating input compensation type differential scanning calorimeter, for example, DSC-7 manufactured by Perkin Elmer Co., may be employed. The measurement method is carried out according to ASTM D3418-82. In the present invention, in the case of measuring the glass transition temperature Tg, it is preferable that a measurement sample is once heated to cancel the entire hysteresis and then quenched and again heated at a heating rate of 10° C./min to employ the DSC curve measured during the heating from 0 to 200° C.

(Image Formation Method)

The electrostatic latent image developing toner of the present invention having the configuration described above is particularly preferably applied to an image formation method comprising at least an charging step of applying a voltage to a charge member from the outside to charge an electrostatic latent image carrier, a step of forming an electrostatic latent image on the charged electrostatic latent image carrier, a development step of developing the electrostatic latent image by the toner to form a toner image on the electrostatic latent image carrier, a transfer step of transferring the toner image on the electrostatic latent image carrier to an object recording material, and a heat-fixation step of heat-fixing the toner image on the object recording material, or an image formation method with the transfer step consisting of a first transfer step of transferring the toner image on the electrostatic latent image carrier to an intermediate transfer body and a second transfer step of transferring the toner image on the intermediate transfer body to the object recording material.

The present invention provides an innovative polyhydroxyalkanoate with a sulfonic group as a hydrophilic group and its derivative introduced therein and a method of producing the same. In this way, the innovative polyhydroxyalkanoate is excellent in melt-processability, and also excellent in biocompatibility owing to its hydrophilic nature, and can thus be expected to be applied as medical flexible members and the like.

In addition, as described above and below, according to the present invention, addition of one or more types of compounds presented in the present invention to an electrostatic latent image developing toner composition as a charge controlling agent makes it possible to provide an electrostatic latent image developing toner having an excellent electrifiability, improving the dispersibility of the compound in the toner resin and the spent characteristic thereof, causing no image fog even when the image is outputted in the image forming apparatus, and being excellent in transferability and highly applicable to an electrophotographic process. In addition, because the charge controlling agent for use in the present invention is colorless or only weakly colored, any coloring agent can be selected according to the color required for the color toner, and the original color of a dye or pigment is not hindered.

EXAMPLES

The present invention will be described further in detail below with reference to Examples, although the method of the present invention should not be limited to the Examples.

First, the method of producing sodium 2-(2'-mercaptoethyl)amide-2-methylpropanesulfonate of formula (24)

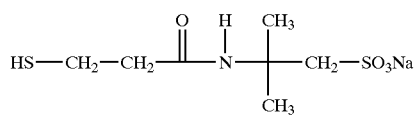

(24)

as one of compounds each expressed by chemical formula (19) will be described.

15.2 g of 2-acrylamide-2-methylpropanesulfonic acid, 2.8 g of sodium hydrate and 0.01 g of benzoyl peroxide were dissolved in 48.5 g of methanol at a room temperature, and gas in the system was replaced with nitrogen. Then, 26.7 g of thioacetic acid was added while maintaining the temperature in the system at 15 to 19° C., and the mixture was thereafter left under reflux for 4 hours, holding the system at the temperature of 45 to 60° C. After cooling, 600 g of isopropyl ether was added to wash the mixture. The insoluble matter was dried so that the weight thereof was reduced to 22 g. The obtained insoluble matter was dissolved in 66 g of methanol at a room temperature, and gas in the system was replaced with nitrogen, 0.76 g of sodium hydrate was added, and was stirred for 3 hours with the temperature in the system being kept at 39 to 41° C. After cooling, 1.2 g of acetic acid was added, and thereafter the solvent was distilled away to obtain thiolated 2-acrylamide-2-methylpropanesulfonic acid. Furthermore, the $^1$H-NMR spectrum was used to ensure that the thiolation had been done in a quantitative manner.

The following Examples 1 to 4 are examples of methods of producing the polyhydroxyalkanoate of the present invention using as a raw material 2-(2'-mercaptoethyl)amide-2-methylpropanesulfonate obtained in the above manner and the polyhydroxyalkanoate produced by the method of production by microorganism described previously. However, the polyhydroxyalkanoate and the method of producing the same should not be solely dependent on the above raw materials.

Example 1

Method (1) of Producing Polyhydroxyalkanoate Containing Units Expressed by Chemical Formulas (25) and (26)

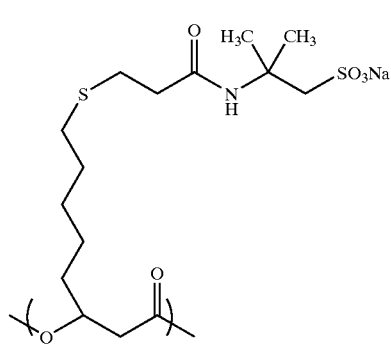

(25)

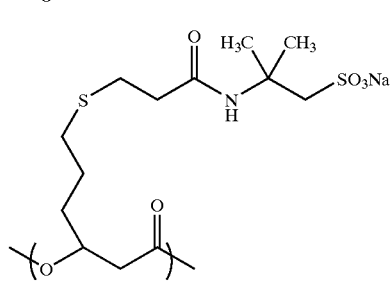

(26)

900 mg of polyhydroxyalkanoate (average molecular weight: Mn=36000, Mw=66000 (measured by gel permeation chromatography (GPC); Tosoh HLC-8220, column: Tosoh TSK-GEL SuperHM-H, solvent: chloroform, polystyrene equivalent)) containing 9.5 mol % in total of 3-hydroxy-8-bromooctanoic acid unit and 3-hydroxy-6-bromohexanoic acid unit, 89.1 mol % of 3-hydroxy-5-phenylvaleric acid and 1.4 mol % of other components (straight-chain 3-hydroxyalkanoic acid having 4 to 12 carbon atoms and straight-chain 3-hydroxyalka-5-enoic acid having 10 or 12 carbon atoms) was dissolved in 12 ml of N,N-dimethylformamide at a room temperature, and gas in the system was replaced with nitrogen. Then, while holding the system at a room temperature, 825 mg of sodium 2-(2'-mercaptoethyl)amide-2-methylpropanesulfonate dissolved in 18 ml of N,N-dimethylformamide was added, and 330 μl of diethylamine was further added, and was stirred at a room temperature for 24 hours.

After the reaction was completed, the mixture was put in 300 ml of diethyl ether to allow reprecipitation for removing N,N-dimethylformamide as a reaction liquid. The resulting precipitate was collected by centrifugal separation.

This precipitate was put in 300 ml of water, stirred and washed. The precipitate obtained at this time was collected by carrying out centrifugal separation. This precipitate was dried under reduced pressure to obtain 244 mg of polyhydroxyalkanoate.

This PHA was analyzed using nuclear magnetic resonance apparatus under the following conditions.
Measuring Apparatus
  FT-NMR: Bruker DPX400
  resonance frequency: $^1$H=400 MHz
Measuring Apparatus
  nuclear species to be measured: $^1$H
  solvent used: DMSO-d6
  reference: capillary-encapsulated DMSO-d6
  measuring temperature: 40° C.

The $^1$H-NMR spectrum chart is shown in FIG. 1, and the composition of PHA calculated from the results obtained by the $^1$H-NMR spectrum is shown in Table 1.

TABLE 1

| | Content of each unit (mol %) |
|---|---|
| Chemical formulas (25) and (26) | 4.8 |
| Chemical formula (27) | 93.0 |
| Other polyhydroxyalkanoate | 2.2 |

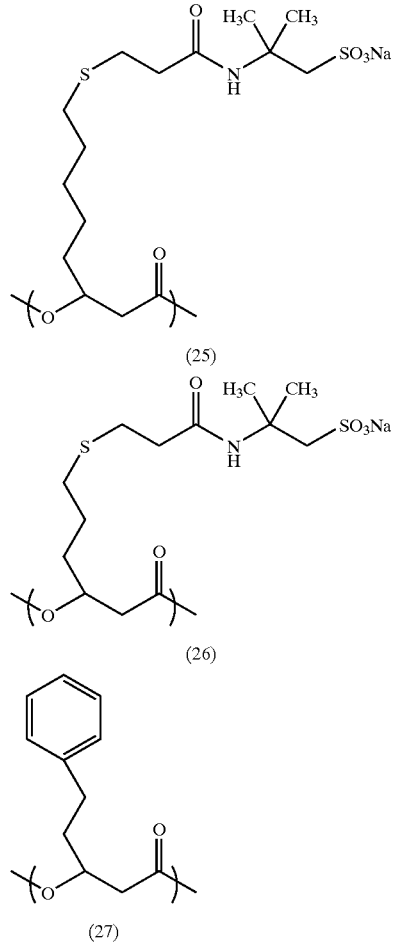

(25)

(26)

(27)

From the results, this polyhydroxyalkanoate was found to contain 4.8 mol % in total of units expressed by chemical formulas (25) and (26) and 93.0 mol % of 3-hydroxy-5-phenylvaleric acid unit expressed by chemical formula (27).

The molecular weight of the obtained PHA was measured by gel permeation chromatography (GPC; Tosoh HLC-8220, column: Tosoh TSK-GEL SuperHM-H, solvent; chloroform, polystyrene equivalent) and found as follows: Mn=10000 and Mw=19400.

Example 2

Method (2) of Producing Polyhydroxyalkanoate Containing Units Expressed by Chemical Formulas (25) and (26)

869 mg of polyhydroxyalkanoate (average molecular weight: Mn=30800, Mw=65200 measured by the gel permeation chromatography described in Example 1) containing 7.4 mol % in total of 3-hydroxy-8-bromooctanoic acid unit and 3-hydroxy-6-bromohexanoic acid, 87.1 mol % of 3-hydroxy-5-phenoxyvaleric acid and 5.5 mol % of other components (straight-chain 3-hydroxyalkanoic acid having 4 to 12 carbon atoms and straight-chain 3-hydroxyalka-5-enoic acid having 10 or 12 carbon atoms) was dissolved in 9 ml of N,N-dimethylformamide at a room temperature, and gas in the system was replaced with nitrogen. Then, while holding the system at a room temperature, 2080 mg of sodium 2-(2'-mercaptoethyl)amide-2-methylpropanesulfonate dissolved in 16 ml of N,N-dimethylformamide was added, and 206 μl of diethylamine was then added, and was stirred at a room temperature for 24 hours.

After the reaction was completed, N,N-dimethylformamide as a reaction liquid was once distilled away by a rotary evaporator, and the mixture was again dissolved in 3 ml of N,N-dimethylformamide, and was thereafter put in 300 ml of pure water to allow reprecipitation. The resulting precipitate was collected by centrifugal separation. This precipitate was suspended again with 50 ml of pure water, and subjected to centrifugal separation to collect the precipitate for washing. This washing operation was conducted three times, followed by drying the precipitate under reduced pressure to obtain 819 mg of polyhydroxyalkanoate.

For this PHA, measurements were carried out using the nuclear magnetic resonance apparatus under the same condition as Example 1.

The composition of PHA calculated from the results obtained by the $^1$H-NMR spectrum is shown in Table 2.

TABLE 2

| | Content of each unit (mol %) |
|---|---|
| Chemical formulas (25) and (26) | 4.0 |
| Chemical formula (28) | 91.0 |
| Other polyhydroxyalkanoate | 5.0 |

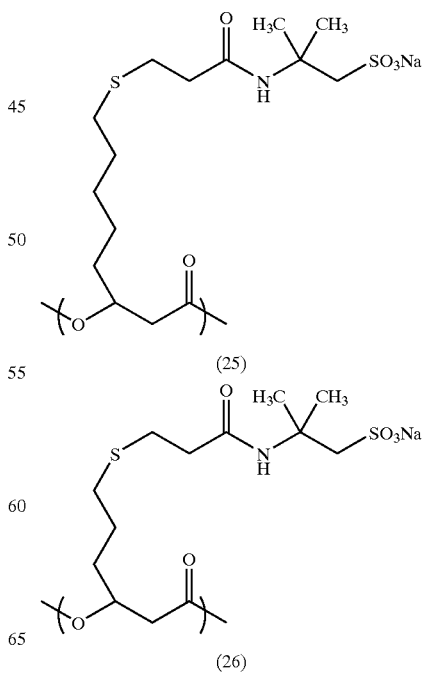

(25)

(26)

TABLE 2-continued

Content of each unit (mol %)

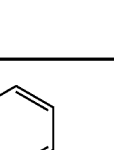

(28)

From the results, this polyhydroxyalkanoate was found to contain 4.0 mol % in total of units expressed by chemical formulas (25) and (26) and 91.0 mol % of 3-hydroxy-5-phenoxyvaleric acid unit expressed by chemical formula (28).

The molecular weight of the obtained PHA was measured by the method described in Example 1 using gel permeation chromatography and found as follows: Mn=3100 and Mw=9100.

Example 3

Method (1) of Producing Polyhydroxyalkanoate Containing Units Expressed by Chemical Formulas (29), (30) and (31)

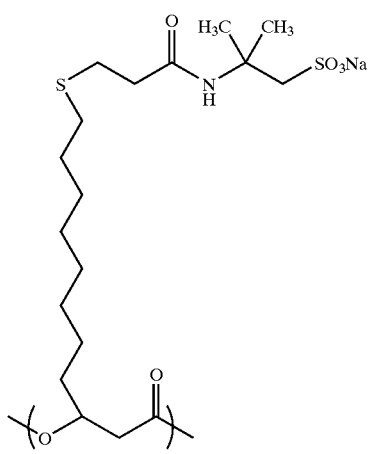

449 mg of polyhydroxyalkanoate (average molecular weight: Mn=48000, Mw=111000 measured by the gel permeation chromatography described in Example 1) containing 7.1 mol % in total of 3-hydroxy-11-bromoundecanoic acid unit, 3-hydroxy-9-bromononanoic acid unit and 3-hydroxy-7-bromoheptanoic acid, 79.3 mol % of 3-hydroxy-5-phenoxyvaleric acid and 13.7 mol % of other components (straight-chain 3-hydroxyalkanoic acid having 4 to 12 carbon atoms and straight-chain 3-hydroxyalka-5-enoic acid having 10 or 12 carbon atoms) was dissolved in 6 ml of N,N-dimethylformamide at a room temperature, and gas in the system was replaced with nitrogen. Then, while holding the system at a room temperature, 265 mg of sodium 2-(2'-mercaptoethyl)amide-2-methylpropanesulfonate dissolved in 8 ml of N,N-dimethylformamide was added, and 106 µl of diethylamine was then added, and was stirred at a room temperature for 24 hours.

After the reaction was completed, N,N-dimethylformamide as a reaction liquid was once distilled away by a rotary evaporator, and the mixture was again dissolved in 2 ml of N,N-dimethylformamide, and was thereafter put in 200 ml of pure water to allow reprecipitation. The resulting precipitate was collected by centrifugal separation. This precipitate was suspended again with 50 ml of pure water, and subjected to centrifugal separation to collect the precipitate for washing. This washing operation was conducted three times, followed by drying the precipitate under reduced pressure to obtain 389 mg of polyhydroxyalkanoate.

For this PHA, measurements were carried out using the nuclear magnetic resonance apparatus under the same condition as Example 1.

The composition of PHA calculated from the results obtained by the $^1$H-NMR spectrum is shown in Table 3.

TABLE 3

| | Content of each unit (mol %) |
|---|---|
| Chemical formulas (29), (30) and (31) | 2.1 |
| Chemical formula (28) | 85.3 |
| Other polyhydroxyalkanoate | 12.6 |

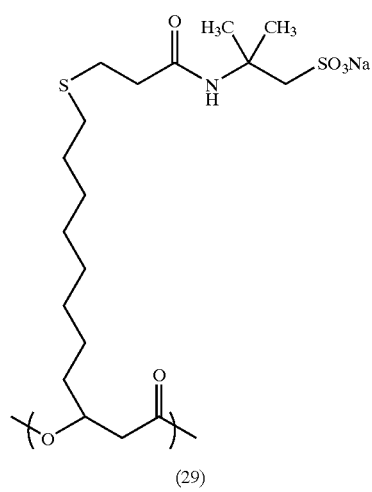

(29)

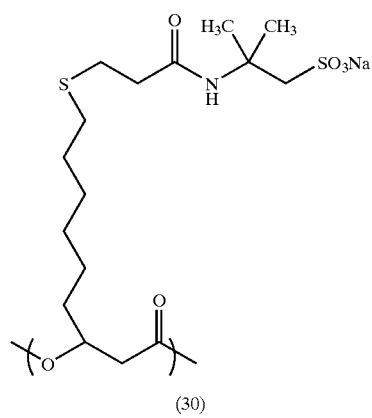

(30)

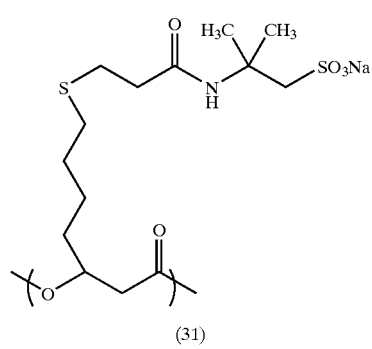

(31)

TABLE 3-continued

| | Content of each unit (mol %) |
|---|---|

(28)

From the results, this polyhydroxyalkanoate was found to contain 2.1 mol % in total of units expressed by chemical formulas (29), (30) and (31) and 85.3 mol % of 3-hydroxy-5-phenoxyvaleric acid unit expressed by chemical formula (28).

The molecular weight of the obtained PHA was measured by the method described in Example 1 using gel permeation chromatography and found as follows: Mn=3400 and Mw=14500.

Example 4

Method (2) of Producing Polyhydroxyalkanoate Containing Units Expressed by Chemical Formulas (29), (30) and (31)

(29)

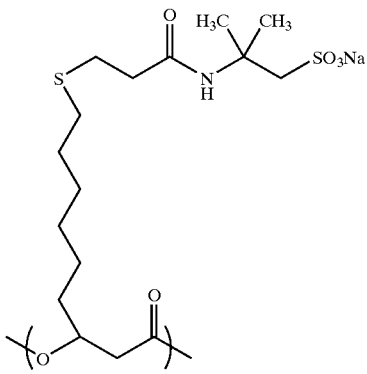

(30)

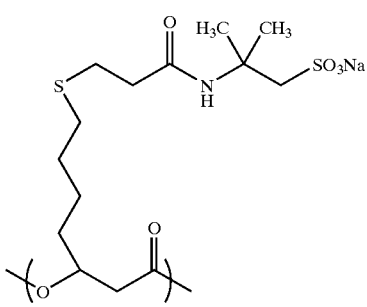

(31)

300 mg of polyhydroxyalkanoate containing 22.0 mol % in total of 3-hydroxy-11-bromoundecanoic acid unit, 3-hydroxy-9-bromononanoic acid unit and 3-hydroxy-7-bromoheptanoic acid, 69.0 mol % of 3-hydroxy-5-(phenylsulfonyl)valeric acid and 9.0 mol % of other components (straight-chain 3-hydroxyalkanoic acid having 4 to 12 carbon atoms and straight-chain 3-hydroxyalka-5-enoic acid having 10 or 12 carbon atoms) was dissolved in 4 ml of N,N-dimethylformamide at a room temperature, and gas in the system was replaced with nitrogen. Then, while holding the system at a room temperature, 446 mg of sodium 2-(2'-mercaptoethyl)amide-2-methylpropanesulfonate dissolved in 6 ml of N,N-dimethylformamide was added, and 180 µl of diethylamine was then added, and was stirred at a room temperature for 18 hours.

After the reaction was completed, N,N-dimethylformamide as a reaction liquid was once distilled away by a rotary evaporator, and the mixture was again dissolved in 2 ml of N,N-dimethylformamide, and was thereafter put in 200 ml of pure water to allow reprecipitation. The resulting precipitate was collected by centrifugal separation. This precipitate was suspended again with 50 ml of pure water, and subjected to centrifugal separation to collect the precipitate for washing. This washing operation was conducted three times, followed by drying the precipitate under reduced pressure to obtain 227 mg of polyhydroxyalkanoate.

For this PHA, measurements were carried out using the nuclear magnetic resonance apparatus under the same condition as Example 1.

The composition of PHA calculated from the results obtained by the $^1$H-NMR spectrum is shown in Table 4.

TABLE 4

|  | Content of each unit (mol %) |
| --- | --- |
| Chemical formulas (29), (30) and (31) | 2.7 |
| Chemical formula (32) | 70.6 |
| Other polyhydroxyalkanoate | 26.7 |

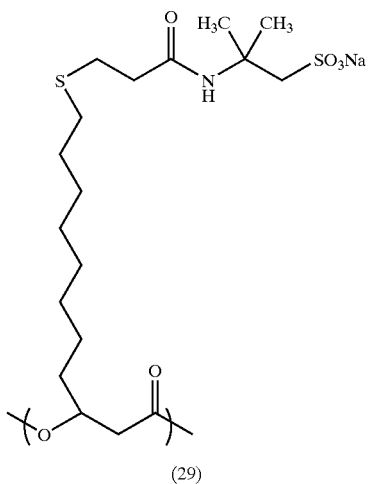

(29)

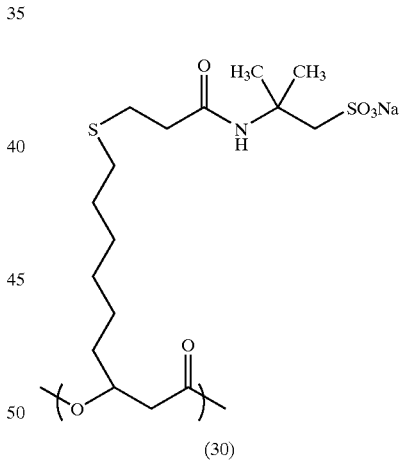

(30)

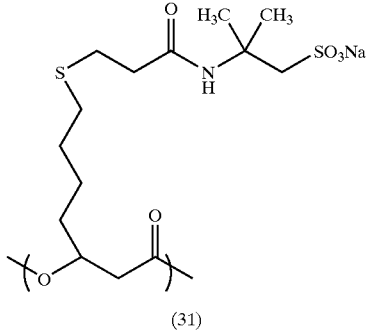

(31)

TABLE 4-continued

Content of each unit (mol %)

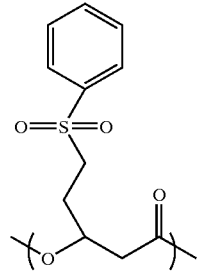

(32)

From the results, this polyhydroxyalkanoate was found to contain 2.7 mol % in total of units expressed by chemical formulas (29), (30) and (31) and 70.6 mol % of 3-hydroxy-5-(phenylsulfonyl)valeric acid unit expressed by chemical formula (32).

The PHA obtained in Examples 1 to 3 described above, which was classified into exemplary compounds (1) to (3) as shown in Table 5, was used as a charge controlling agent to produce various kinds of toners, and evaluations were carried out (Examples 5 to 44).

TABLE 5

| Exemplary compound (1) | PHA of Example 1 |
| Exemplary compound (2) | PHA of Example 2 |
| Exemplary compound (3) | PHA of Example 3 |

Example 5

First, an aqueous $Na_3PO_4$ solution was added in a 2 liter four-necks flask equipped with a high-speed stirring apparatus TK-Homomixer, and was heated at 60° C. with the number of rotations kept at 10,000 rpm. An aqueous $CaCl_2$ solution was slowly added therein to prepare an aqueous dispersing medium containing a very small water slightly soluble dispersant $Ca_3(PO_4)_2$.

On the other hand, the following compositions were dispersed for 3 hours using a ball mill, followed by adding therein 10 parts by weight of release agent (ester wax) and 10 parts by weight of 2,2'-azobis(2,4-dimethylvaleronitrile) as a polymerization initiator to prepare a polymerizable monomer composition.

| styrene monomer | 82 parts by weight |
| ethylhexyl acrylate monomer | 18 parts by weight |
| divinylbenzene monomer | 0.1 parts by weight |
| cyan coloring agent (C. I. Pigment Blue 15) | 6 parts by weight |
| oxidized polyethylene resin (molecular weight 3200, acid number 8) | 5 parts by weight |
| exemplary compound (1) | 2 parts by weight |

Then, the polymerizable monomer composition obtained as described above was put in the aqueous dispersing medium prepared previously to carry out the granulation with the number of rotations being kept at 10,000 rpm. Thereafter, the composition was made to undergo a reaction at 65° C. for 3 hours while being stirred with a paddle stirring blade, and was thereafter polymerized at 80° C. for 6 hours to complete the polymerization reaction. After the reaction was completed, the suspension was cooled, and an acid was added therein to dissolve the water slightly soluble dispersant $Ca_3(PO_4)_2$, followed by filtering, rinsing and drying the solution to obtain blue polymerized particles (1). The particle size of the obtained blue polymerized particles (1) measured using Coulter Counter Multisizer (manufactured by Coulter Co.) was 7.1 μm as a weight average particle size, and the ratio of fines (the abundance ratio of particles with the size of 3.17 μm or smaller in the number distribution) was 5.5% by number.

As a fluidity improver, 1.3 parts by weight of hydrophobic silica fine powder (BET: 270 $m^2/g$) treated with hexamethyl disilazane were externally added to 100 parts by weight of blue polymerized particles (1) prepared as described above through dry-mixing by a Henshel mixer, whereby a blue toner (1) of this Example was obtained. In addition, 7 parts by weight of blue toner (1) were mixed with 93 parts by weight of resin-coated magnetic ferrite carrier (average particle size: 45 μm) to prepare a two-component type blue developer (1) for magnetic brush development.

Examples 6 and 7

Blue toners (2) and (3) of Examples 6 and 7 were obtained in the same manner as Example 5 except that 2.0 part by weight of exemplary compounds (2) and (3) are used, respectively, in place of exemplary compound (1). In addition, two-component type blue developers (2) and (3) were obtained, respectively, in the same manner as Example 5 using the blue toners (2) and (3) and the above described resin-coated magnetic ferrite carrier. For these blue toners (2) and (3) as well as the two-component type blue developers (2) and (3), the properties of toners were measured in the same manner as Example 5, and the results thereof are shown in Table 6.

Comparative Example 1

A blue toner (4) of Comparative Example 1 was obtained in the same manner as Example 5 except that no charge controlling agent was used. The properties of this toner were measured in the same manner as Example 5, and the results thereof are shown in Table 6. In addition, a two-component type blue developer (4) of Comparative Example 1 was obtained in the same manner as Example 5 using this toner.

Evaluation

For the two-component type blue developers (1) to (3) obtained in the Examples 5 to 7 and the two-component type blue developer (4) obtained in the Comparative Example 1, the charge levels of toners after stirring for 10 and 300 seconds were measured under conditions of normal temperature and normal humidity (25° C., 60% RH) and high temperature and high humidity (30° C., 80% RH) using the previously described method of measuring charge levels. Then, measurement values of two-component blow-off charge levels were rounded off to the first decimal place, and the resultant values were evaluated according to the following criteria. The results are shown together in Table 6.

Electrifiability

A: Excellent (−20 μC/g or lower)
B: Good (−19.9 to −10.0 μC/g)
C: Usable (−9.9 to −5.0 μC/g)
D: Unusable (−4.9 μC/g or higher)

TABLE 6

| Examples | Toners Number: Blue | Particle size distribution Weight average particle size (μm) | Ratio of fines (% by number) | Electrifiability Normal temperature and normal humidity (Q/M) Stirring for 10 seconds | Stirring for 300 seconds | High temperature and high humidity (Q/M) Stirring for 10 seconds | Stirring for 300 seconds |
|---|---|---|---|---|---|---|---|
| 5 | 1 | 7.1 | 5.5 | A | A | A | A |
| 6 | 2 | 7.2 | 5.3 | A | A | A | A |
| 7 | 3 | 7.0 | 5.1 | B | A | B | A |
| Comparative Example 1 | 4 | 7.0 | 5.2 | D | D | D | D |

Examples 8 to 10

Yellow toners (1) to (3) were obtained in the same manner as Example 5 except that 2.0 parts by weight of exemplary compounds (1) to (3) were used, and a yellow coloring agent (Hansa yellow G) was used in place of the cyan coloring agent. The properties of these toners were measured in the same manner as Example 5, and the results thereof are shown in Table 7. In addition, two-component type yellow developers (1) to (3) were obtained in the same manner as Example 5 using these toners.

Comparative Example 2

A yellow toner (4) of Comparative Example 2 was obtained in the same manner as Example 5 except that no charge controlling agent was used, and that the yellow coloring agent (Hansa yellow G) was used in place of the cyan coloring agent. The properties of this toner were measured in the same manner as Example 5, and the results thereof are shown in Table 7. In addition, a two-component type yellow developer (4) of Comparative Example 2 was obtained in the same manner as Example 5 using this toner.

Evaluation

For the two-component type yellow developers (1) to (3) obtained in the Examples 0.8 to 10 and the two-component type yellow developer (4) obtained in the Comparative Example 2, the charge levels of toners after stirring for 10 and 300 seconds were measured under conditions of normal temperature and normal humidity (25° C., 60% RH) and high temperature and high humidity (30° C., 80% RH) using the previously described method of measuring charge levels.

Then, measurement values of two-component blow-off charge levels were rounded off to the first decimal place, and the resultant values were evaluated according to the following criteria. The results are shown together in Table 7.

Electrifiability

A: Excellent (−20 $\mu$C/g or lower)
B: Good (−19.9 to −10.0 $\mu$C/g)
C: Usable (−9.9 to −5.0 $\mu$C/g)
D: Unusable (−4.9 $\mu$C/g or higher)

TABLE 7

| Examples | Toners Number: Yellow | Particle size distribution Weight average particle size (μm) | Ratio of fines (% by number) | Electrifiability Normal temperature and normal humidity (Q/M) Stirring for 10 seconds | Stirring for 300 seconds | High temperature and high humidity (Q/M) Stirring for 10 seconds | Stirring for 300 seconds |
|---|---|---|---|---|---|---|---|
| 8 | 1 | 7.0 | 5.4 | A | A | A | A |
| 9 | 2 | 7.2 | 5.3 | A | A | A | A |
| 10 | 3 | 6.9 | 5.5 | B | A | B | B |
| Comparative Example 2 | 4 | 7.2 | 4.9 | D | D | D | D |

Examples 11 to 13

Black toners (1) to (3) of were obtained in the same manner as Example 5 using 2.0 parts by weight of exemplary compounds (1) to (3) except that a carbon black (DBP oil absorption 110 mL/100 g) was used in place of the cyan coloring agent. The properties of these toners were measured in the same manner as Example 5, and the results thereof are shown in Table 8. In addition, two-component type black developers (1) to (3) were obtained in the same manner as Example 5 using these toners.

Comparative Example 3

A black toner (4) of Comparative Example 3 was obtained in the same manner as Example 5 except that no charge controlling agent was used and that the carbon black (DBP oil absorption 110 mL/100 g) was used in place of the cyan coloring agent. The properties of this toner were measured in the same manner as Example 5, and the results thereof are shown in Table 8. In addition, a two-component type black developer (4) of Comparative Example 3 was obtained in the same manner as Example 5 using this toner.

Evaluation

For the two-component type black developers (1) to (3) obtained in the Examples 11 to 13 and the two-component type black developer (4) obtained in the Comparative Example 3, the charge levels of toners after stirring for 10 and 300 seconds were measured under conditions of normal temperature and normal humidity (25° C., 60% RH) and high temperature and high humidity (30° C., 80% RH) using the previously described method of measuring charge levels. Then, measurement values of two-component blow-off charge levels were rounded off to the first decimal place, and the resultant values were evaluated according to the following criteria. The results are shown together in Table 8.

Electrifiability

A: Excellent (−20 µC/g or lower)
B: Good (−19.9 to −10.0 µC/g)
C: Usable (−9.9 to −5.0 µC/g)
D: Unusable (−4.9 µC/g or higher)

TABLE 8

| Examples | Toners Number: Black | Particle size distribution | | Electrifiability | | | |
|---|---|---|---|---|---|---|---|
| | | | | Normal temperature and normal humidity (Q/M) | | High temperature and high humidity (Q/M) | |
| | | Weight average particle size (µm) | Ratio of fines (% by number) | Stirring for 10 seconds | Stirring for 300 seconds | Stirring for 10 seconds | Stirring for 300 seconds |
| 11 | 1 | 7.0 | 5.3 | A | A | A | A |
| 12 | 2 | 7.1 | 5.4 | A | A | A | A |
| 13 | 3 | 6.9 | 5.2 | B | B | B | B |
| Comparative Example 3 | 4 | 6.9 | 5.3 | D | C | D | C |

Example 14

| stylene-butylacrylate copolymer resin (glass transition temperature 70° C.) | 100 parts by weight |
|---|---|
| magenta pigment (C. I. Pigment Red 114) | 5 parts by weight |
| exemplary compound (1) | 2 parts by weight |

The above described compositions were mixed and melt-kneaded by a biaxial extruder (L/D=30). The resulting mixture was cooled and then roughly ground by a hammer mill, and finely being ground by a jet mill. The resultant powder was classified to obtain magenta coloring particles (1). The weight average particle size and the ratio of fines of the magenta coloring particles (1) were 7.0 µm and 5.2% by number.

As a fluidity improver, 1.5 parts by weight of hydrophobic silica fine powder (BET: 250 m²/g) treated with hexamethyl disilazane were dry-mixed with 100 parts by weight of the magenta coloring particles (1) by a Henshel mixer, whereby a magenta toner (1) of this Example was obtained. In addition, 7 parts by weight of the resulting magenta toner (1) were mixed with 93 parts by weight of resin-coated magnetic ferrite carrier (average particle size: 45 µm) to prepare a two-component type magenta developer (1) for magnetic brush development. The properties of this toner were measured in the same manner as Example 5, and the results thereof are shown in Table 9.

Examples 15 and 16

Magenta toners (2) and (3) of Examples 15 and 16 were obtained in the same manner as Example 14 except that 2.0 parts by weight of each of exemplary compounds (2) and (3) were used in place of exemplary compound (1). The properties of these toners were measured in the same manner as Example 5, and the results thereof are shown in Table 9. In addition, two-component type magenta developers (2) and (3) were obtained in the same manner as Example 14 using these toners.

Comparative Example 4

A magenta toner (4) of Comparative Example 4 was obtained in the same manner as Example 14 except that no charge controlling agent was used. The properties of this toner were measured in the same manner as Example 5, and the results thereof are shown in Table 9. In addition, a two-component type magenta developer (4) of Comparative Example 4 was obtained in the same manner as Example 14 using this toner.

Evaluation

For the two-component type magenta developers (1) to (3) obtained in the Examples 14 to 16 and the two-component type magenta developer (4) obtained in the Comparative Example 4, the charge levels of toners after stirring for 10 and 300 seconds were measured under conditions of normal temperature and normal humidity (25° C., 60% RH) and high temperature and high humidity (30° C., 80% RH) using the previously described method of measuring charge levels. Then, measurement values of two-component blow-off charge levels were rounded off to the first decimal place, and the resultant values were evaluated according to the following criteria. The results are shown together in Table 9.

Electrifiability

A: Excellent (−20 µC/g or lower)
B: Good (−19.9 to −10.0 µC/g)
C: Usable (−9.9 to −5.0 µC/g)
D: Unusable (−4.9 µC/g or higher)

TABLE 9

| Examples | Toners Number: Red | Particle size distribution Weight average particle size (μm) | Ratio of fines (% by number) | Electrifiability Normal temperature and normal humidity (Q/M) Stirring for 10 seconds | Stirring for 300 seconds | High temperature and high humidity (Q/M) Stirring for 10 seconds | Stirring for 300 seconds |
|---|---|---|---|---|---|---|---|
| 14 | 1 | 7.0 | 5.2 | A | A | A | A |
| 15 | 2 | 7.1 | 5.1 | A | A | A | A |
| 16 | 3 | 6.9 | 5.3 | B | A | B | A |
| Comparative Example 4 | 4 | 7.1 | 5.1 | D | C | D | C |

Examples 17 to 19

Black toners (5) to (7) were obtained in the same manner as Example 14 using 2.0 parts by weight of exemplary compounds (1) to (3) except that a carbon black (DBP oil absorption 110 mL/100 g) was used in place of the magenta pigment. The properties of these toners were measured in the same manner as Example 5, and the results thereof are shown in Table 10. In addition, two-component type black developers (5) to (7) were obtained in the same manner as Example 14 using these toners.

charge levels were rounded off to the first decimal place, and the resultant values were evaluated according to the following criteria. The results are shown together in Table 10.

Electrifiability

A: Excellent (−20 $\mu$C/g or lower)
B: Good (−19.9 to −10.0 $\mu$C/g)
C: Usable (−9.9 to −5.0 $\mu$C/g)
D: Unusable (−4.9 $\mu$C/g or higher)

TABLE 10

| Examples | Toners Number: Black | Particle size distribution Weight average particle size (μm) | Ratio of fines (% by number) | Electrifiability Normal temperature and normal humidity (Q/M) Stirring for 10 seconds | Stirring for 300 seconds | High temperature and high humidity (Q/M) Stirring for 10 seconds | Stirring for 300 seconds |
|---|---|---|---|---|---|---|---|
| 17 | 5 | 7.1 | 5.4 | A | A | A | A |
| 18 | 6 | 7.0 | 5.3 | A | A | A | A |
| 19 | 7 | 6.9 | 5.2 | B | A | B | B |
| Comparative Example 5 | 8 | 7.0 | 5.7 | D | C | D | D |

Comparative Example 5

A black toner (8) of Comparative Example 5 was obtained in the same manner as Example 14 except that no charge controlling agent was used and that the carbon black (DBP oil absorption 110 mL/100 g) was used in place of the magenta pigment. The properties of this toner were measured in the same manner as Example 5, and the results thereof are shown in Table 10. In addition, a two-component type black developer (8) of Comparative Example 5 was obtained in the same manner as Example 14 using this toner.

Evaluation

For the two-component type black developers (5) to (7) obtained in the Examples 17 to 19 and the two-component type black developer (8) obtained in the Comparative Example 5, the charge levels of toners after stirring for 10 and 300 seconds were measured under conditions of normal temperature and normal humidity (25° C., 60% RH) and high temperature and high humidity (30° C., 80% RH) using the previously described method of measuring charge levels. Then, measurement values of two-component blow-off

Example 20

| | |
|---|---|
| polyester resin | 100 parts by weight |
| carbon black (DBP absorption 110 ml/100 g) | 5 parts by weight |
| exemplary compound (1) | 2 parts by weight |

The polyester resin was synthesized as follows: 751 parts of bisphenol A propylene oxide 2 mol adduct, 104 parts of terephtalic acid and 167 parts of trimellitic anhydride were polycondensed with two parts of dibutyltin oxide as a catalyst to obtain a polyester resin having a softening point of 125° C.

The above described compositions were mixed and melt-kneaded by a biaxial extruder (L/D=30). The resulting mixture was cooled and then roughly ground by a hammer mill, and finely ground by a jet mill. The resultant powder was classified to obtain black coloring particles (9). The weight average particle size and the ratio of fines of the black coloring particles (9) were 7.7 μm and 5.0% by number.

As a fluidity improver, 1.5 parts by weight of hydrophobic silica fine powder (BET: 250 m²/g) treated with hexamethyl disilazane were dry-mixed with 100 parts by weight of the black coloring particles (9) by a Henshel mixer, whereby a Electrifiability A: Excellent (−20 μC/g or lower)
B: Good (−19.9 to −10.0 μC/g)
C: Usable (−9.9 to −5.0 μC/g)
D: Unusable (−4.9 μC/g or higher)

TABLE 11

| Examples | Toners Number: Black | Particle size distribution | | Electrifiability | | | |
|---|---|---|---|---|---|---|---|
| | | | | Normal temperature and normal humidity (Q/M) | | High temperature and high humidity (Q/M) | |
| | | Weight average particle size (μm) | Ratio of fines (% by number) | Stirring for 10 seconds | Stirring for 300 seconds | Stirring for 10 seconds | Stirring for 300 seconds |
| 20 | 9 | 7.7 | 5.0 | A | A | A | A |
| 21 | 10 | 7.6 | 4.9 | A | A | A | A |
| 22 | 11 | 7.4 | 5.2 | B | B | B | A |
| Comparative Example 6 | 12 | 7.5 | 4.9 | D | C | D | C | black toner (9) of this Example was obtained. In addition, 7 parts by weight of the resulting black toner (9) were mixed with 93 parts by weight of resin-coated magnetic ferrite carrier (average particle size: 45 μm) to prepare a two-component type black developer (9) for magnetic brush development. The properties of this toner were measured in the same manner as Example 5, and the results thereof are shown in Table 11.

Examples 21 and 22

Black toners (10) and (11) of Examples 21 and 22 were obtained in the same manner as Example 20 except that 2.0 parts by weight of each of exemplary compounds (2) and (3) were used in place of exemplary compound (1). The properties of these toners were measured in the same manner as Example 5, and the results thereof are shown in Table 11. In addition, two-component type black developers (10) and (11) were obtained in the same manner as Example 20 using these toners.

Comparative Example 6

A black toner (12) of Comparative Example 6 was obtained in the same manner as Example 20 except that no exemplary compound (1) was used. The properties of this toner were measured in the same manner as Example 5, and the results thereof are shown in Table 11. In addition, a two-component type black developer (12) of Comparative Example 6 was obtained in the same manner as Example 20 using this toner.

Evaluation

For the two-component type black developers (9) to (11) obtained in the Examples 20 to 22 and the two-component type black developer (12) obtained in the Comparative Example 6, the charge levels of toners after stirring for 10 and 300 seconds were measured under conditions of normal temperature and normal humidity (25° C., 60% RH) and high temperature and high humidity (30° C., 80% RH) using the previously described method of measuring charge levels. Then, measurement values of two-component blow-off charge levels were rounded off to the first decimal place, and the resultant values were evaluated according to the following criteria. The results are shown together in Table 11.

Examples 23 to 40 and Comparative Examples 7 to 12

Figure 2:
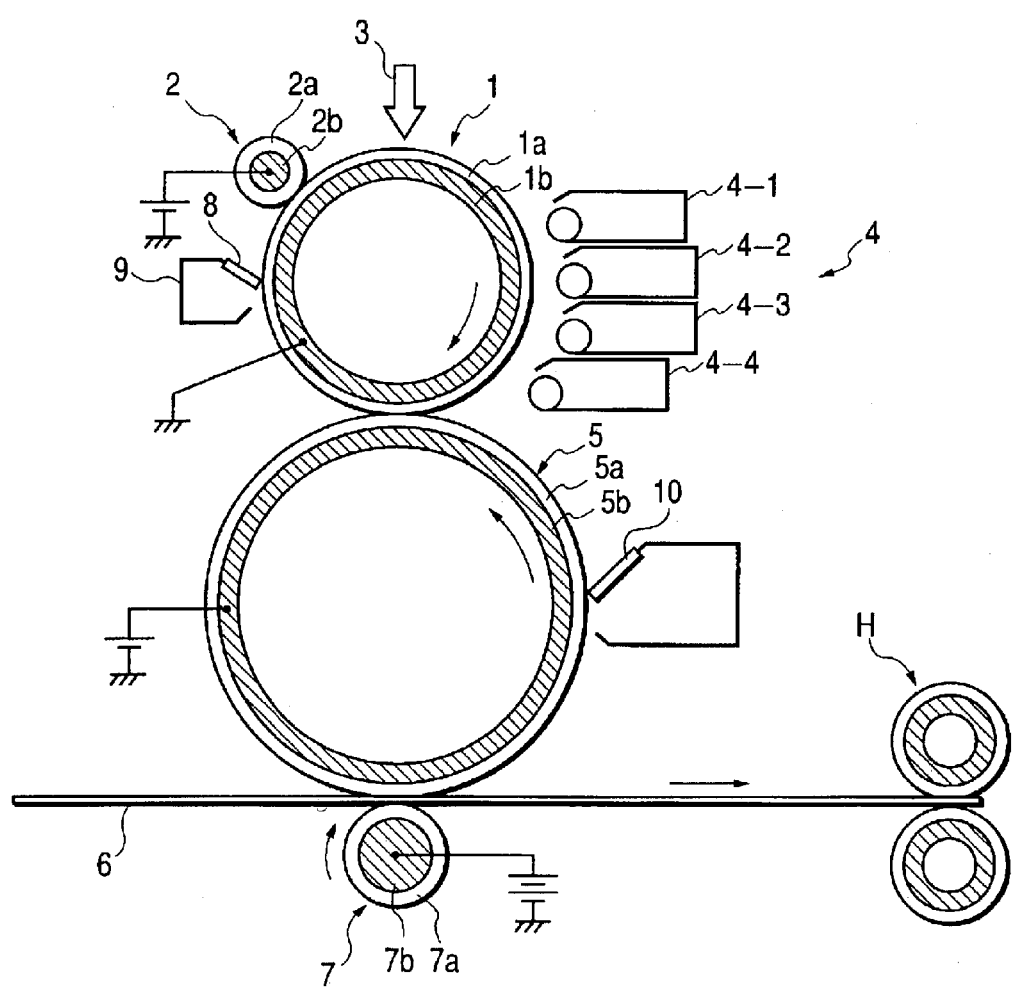
FIG. 2 is a schematic explanatory view of an image forming apparatus used in Examples 23 to 40 and Comparative Examples 7 to 12.

First, an image forming apparatus used in the image formation methods of Examples 23 to 40 and Comparative Examples 7 to 12 will be described. FIG. 2 is a schematic explanatory view of the cross section of an image forming apparatus for carrying out the image formation methods of Examples and Comparative Examples of the present invention. A photoconductor drum 1 shown in FIG. 2 has a photosensitive layer 1a having an organic photo semiconductor on a substrate 1b, and is configured to rotate in the direction indicated by the arrow, and its surface is electrically charged at a potential of about −600 V by a charge roller 2 being a charge member situated opposite to the photoconductor drum 1 and contacting and rotating with the drum. As shown in FIG. 2, the charge roller 2 has a cored bar 2b covered with a conductive elastic layer 2a.

Figure 3:
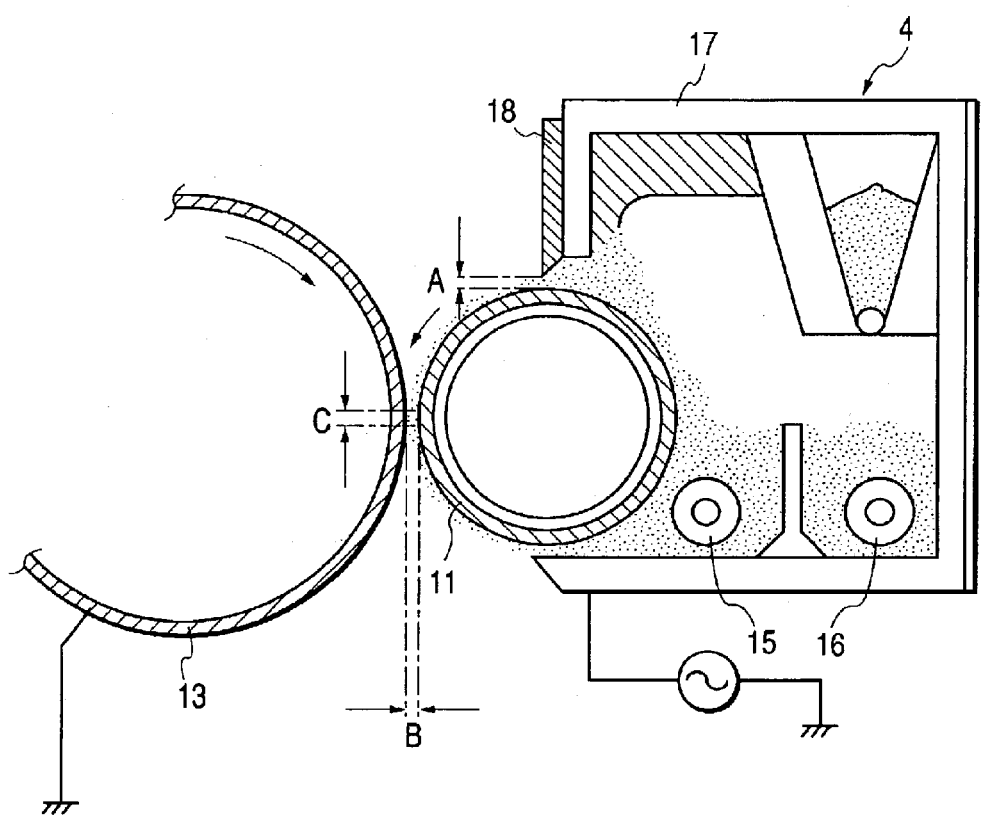
FIG. 3 is a sectional view of a principal part of a development apparatus for a two-component developer used in Examples 23 to 40 and Comparative Examples 7 to 12.

Next, the photoconductor drum 1 with its surface electrically charged is exposed to light 3 and at this time, on/off operations are performed on the photoconductor by a polygon mirror according to digital image information, whereby an electrostatic latent image with the potential of the exposed area being −100 V and the potential of the dark area being −600 V is formed. Subsequently, this electrostatic latent image on the photoconductor drum 1 is reverse-developed and thereby actualized using a plurality of development apparatuses 4-1, 4-2, 4-3 and 4—4, and thus a toner image is formed on the photoconductor drum 1. At this time, the two-component type developers obtained in Examples 5 to 22 and Comparative Examples 1 to 6 were individually used as developers to form a toner image with a yellow toner, a magenta toner, a cyan toner or a black toner. FIG. 3 is an enlarged sectional view of principal parts of development apparatuses 4 for two-component type developers used at that time.

Then, the toner image on the photoconductor drum 1 is transferred to an intermediate transfer body 5 contacting and rotating with the photoconductor drum 1. As a result, a four-color color combination developed image is formed on the intermediate transfer body 5. A non-transferred toner remaining on the photoconductor drum 1 without being transferred is collected in a container 9 for residual toners by a cleaner member 8.

The intermediate transfer body 5 is constituted by a cored bar 5b as a support and an elastic layer 5a provided thereon as shown in FIG. 2. In this Example, the intermediate body 5 having the cored bar 5b coated with the elastic layer 5b with a carbon black as a conductivity producer sufficiently dispersed in nitrile-butadiene rubber (NBR) was used. The degree of hardness of the elastic layer 5b measured in accordance with "JIS K-6301" was 30 degrees, and the volume resistivity was $1 \times 10^9$ Ω·cm. The level of transfer current required for transferring the image from the photoconductor drum 1 to the intermediate transfer body 5 is about 5 μA, and this level of current was obtained by adding a voltage of +500 V to the cored bar 5b.

The four-color toner color combination latent image formed on the intermediate transfer body 5 is transferred to an object transferring material such as a paper by a transfer roller 7, and is thereafter fixed by a heat-fixation apparatus H. The transfer roller 7 is provided thereon the core metal 7b with the outside diameter of 10 mm on which an elastic layer 7a is formed by coating of a foam of ethylene-propylene-diene based tridimensional copolymer (EPDM) dispersing carbon sufficiently therein as a conductivity producing material. The layer had a volume specific resistance of $1 \times 10^6$ Ω·cm and a hardness degree of 35° as measured in accordance with "JIS K-6301". In addition, a voltage was applied to this transfer roller 7 to pass a transfer current of 15 μA therethrough.

Figure 6:
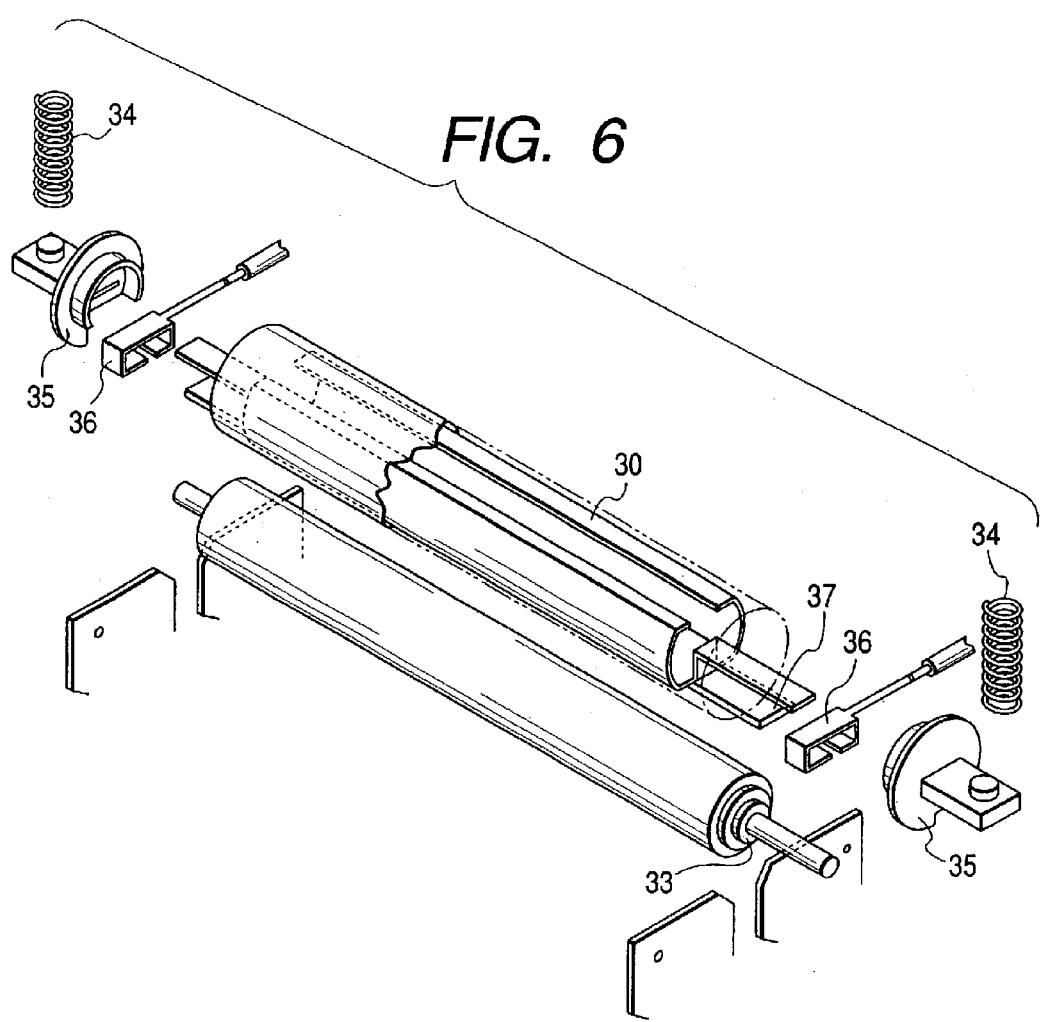
FIG. 6 is an exploded perspective view of a principal part of a fixation apparatus used in the Example of the present invention.
Figure 7:
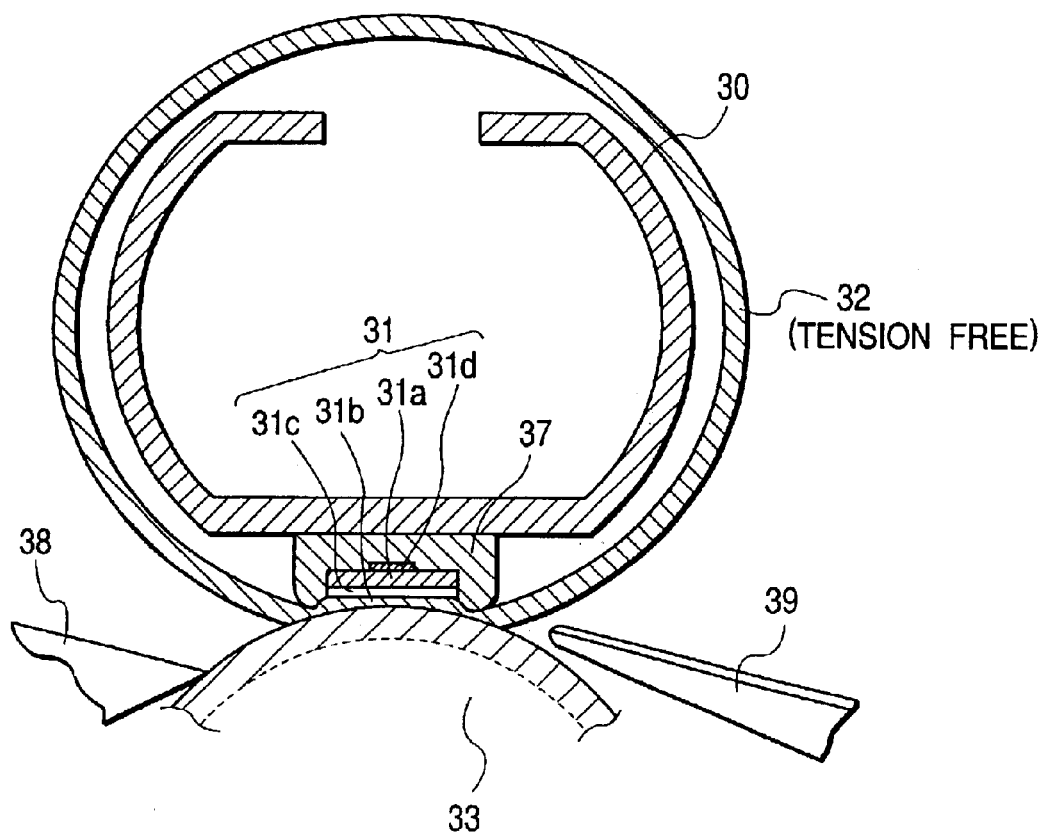
FIG. 7 is an enlarged sectional view of a principal part showing a film state of the fixation apparatus used in the Example of the present invention at the time when it is not driven.

In the apparatus shown in FIG. 2, a fixation apparatus of heated roll type having no oil coating mechanism shown in FIGS. 6 and 7 was used in the heat-fixation apparatus H. The both upper and lower rollers of the fixation apparatus used here had surface layers made of fluorine based resin. In addition, the diameter of the roller was 60 mm. The fixation temperature for fixation was 160° C., and the nipping width was set at 7 mm. Furthermore, a transfer residual toner on the photoconductor drum 1, which was collected by cleaning, was transported to a developing device by a reuse mechanism for reuse.

Evaluation

Two-component type developers produced using the toners of Examples 5 to 22 and two-component type developers produced using toners of Comparative Examples 1 to 6 were used, respectively, to perform printout testing at a printout rate of 8 sheets (A4 size) per minute while the developer was supplied one after another in a monochromatic intermittent mode (namely a mode in which the developing device is stopped for 10 seconds for each printout to accelerate the degradation of a toner in a preliminary operation during restart of the device) at a normal temperature and normal humidity (25° C., 60% RH) and a high temperature and high humidity (30° C., 80% RH) under the conditions described above, and resulting printout images were evaluated for the following items. The evaluation results are shown together in Table 12.

Evaluation of Printout Images

1. Image Density

Images were printed out on a predetermined number of normal copying papers (75 g/m$^2$), and the image density was evaluated according to the level at which the density of the image from the final printout was retained with respect to the density of the initial image. Furthermore, for the measurement of image density, a Macbeth reflective densitometer (manufactured by Macbeth Co., Ltd.) was used to measure a density relative to that of the printout image on a white ground with the density of original copy equal to 0.00.

A: Excellent (image density from the final printout is 1.40 or greater)

B: Good (image density from the final printout is 1.35 or greater and lower than 1.40)

C: Usable (image density from the final printout is 1.00 or greater and lower than 1.35)

D: Unusable (image density from the final printout is lower than 1.00)

2. Image Fog

Images were printed out on a predetermined number of normal copying papers (75 g/m$^2$), and the image fog was evaluated with a solid white image from the final printout. Specifically, the evaluation was made as follow: the worst value of the reflective density of the white ground after printing and the average reflective density of the paper before printing, as measured using a reflective densitometer (Reflectometer ODEL TC-6DS manufactured by Tokyo Denshoku Co., Ltd.), were defined as Ds and Dr, respectively, (Ds-Dr) was calculated from these values as a fog level to make an evaluation according to the following criterion.

A: Excellent (fog level is 0% or higher and lower than 1.5%)

B: Good (fog level is 1.5% or higher and lower than 3.0%)

C: Usable (fog level is 3.0% or higher and lower than 5.0%)

D: Unusable (fog level is 5.0% or higher)

3. Transferability

Solid black images were printed out on a predetermined number of normal copying papers (75 g/m$^2$), and the image dislocation level of the image from the final printout was visually observed to make an evaluation according to the following criterion.

A: Excellent (almost not observed)

B: Good (slightly observed)

C: Usable

D: Unusable

In addition, in Examples 23 to 40 and Comparative Examples 7 to 12, occurrences of scares and sticking residual toners on the surfaces of the photoconductor drum and intermediate transfer body, and their influence on printout images (matching with the image forming apparatus) were visually evaluated after 5000 images were outputted, and as a result, scars and sticking residual toners on the surfaces of the photoconductor drum and intermediate transfer body were not observed, and thus matching with the image forming apparatus was excellent for the system using two-component type developers of Examples 23 to 40. For the system using two-component type developers of Comparative Examples 7 to 12, on the other hand, sticking toners were observed on the surface of the photoconductor drum in all cases. In addition, for the system using two-component type developers of Comparative Examples 7 to 12, sticking toners and surface scars could be observed on the surface of the intermediate transfer body, and there was a problem in matching with image formation apparatus such that longitudinally striped defects occurred on the image.

TABLE 12

| Examples | Two-component type developer | Normal temperature and normal humidity | | | High temperature and high humidity | | |
|---|---|---|---|---|---|---|---|
| | | Image density | Image fog | Transferability | Image density | Image fog | Transferability |
| 23 | Blue 1 | A | A | A | A | A | A |
| 24 | Blue 2 | A | A | A | A | A | A |
| 25 | Blue 3 | B | A | A | B | B | A |
| 26 | Yellow 1 | A | A | A | A | A | A |
| 27 | Yellow 2 | A | A | A | A | A | A |
| 28 | Yellow 3 | B | A | A | B | B | A |
| 29 | Black 1 | A | A | A | A | A | A |
| 30 | Black 2 | A | A | A | A | A | A |
| 31 | Black 3 | A | B | B | B | B | B |
| 32 | Red 1 | A | A | A | A | A | A |
| 33 | Red 2 | A | A | A | A | A | A |
| 34 | Red 3 | A | A | B | B | B | B |
| 35 | Black 5 | A | A | A | A | A | A |
| 36 | Black 6 | A | A | A | A | A | A |
| 37 | Black 7 | B | A | A | B | B | A |
| 38 | Black 9 | A | A | A | A | A | A |
| 39 | Black 10 | A | A | A | A | A | A |
| 40 | Black 11 | B | B | B | B | B | B |
| Comparative Example 7 | Blue 4 | D | D | D | D | D | D |
| Comparative Example 8 | Yellow 4 | D | D | D | D | D | D |
| Comparative Example 9 | Black 4 | C | C | D | C | D | D |
| Comparative Example 10 | Red 4 | C | C | D | C | D | D |
| Comparative Example 11 | Black 8 | C | C | D | D | D | D |
| Comparative Example 12 | Black 12 | C | C | D | C | D | D |

Examples 41 to 43 and Comparative Examples 13 to 15

Figure 4:
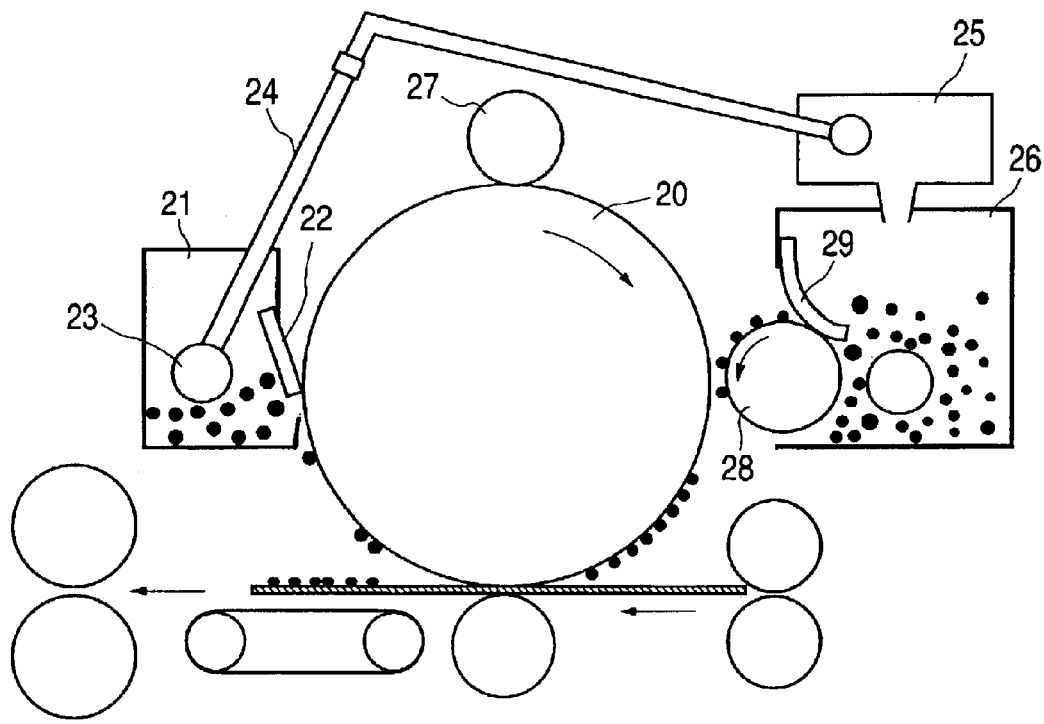
FIG. 4 is a schematic explanatory view having a reuse mechanism of a toner used in Examples 41 to 43 and Comparative Examples 13 to 15.

For carrying out the image formation methods of Examples 41 to 43 and Comparative Examples 13 to 15, the toners obtained in Examples 5, 8 and 11 and Comparative examples 1 to 3 were used, respectively, as developers. In addition, for means for forming an image, an image forming apparatus with a commercially available laser beam printer LBP-EX (manufactured by Canon Inc.) modified so that it was provided with a reuse mechanism and reset as shown in FIG. 4 was used. That is, the image forming apparatus shown in FIG. 4 is provided with a system in which a non-transferred toner remaining on the photoconductor drum 20 after the transfer process is scraped off by an elastic blade 22 of a cleaner 21 abutting against the photoconductor drum 20, then sent into the cleaner 21 by a cleaner roller, passed through a cleaner reuse 23, and returned to the development device 26 via a hopper 25 by a supply pipe 24 with a carrier screw mounted thereon, and the toner collected in this way is reused.

In the image forming apparatus shown in FIG. 4, the surface of the photoconductor drum 20 is electrically charged by a primary charge roller 27. A rubber roller (diameter 12 mm, abutment pressure 50 g/cm) coated with a nylon resin and having conductive carbon dispersed therein was used for the primary charge roller 27, and an electrostatic latent image with a dark area potential VD of −700 V and a light area potential VL of −200 V was formed on the electrostatic latent image carrier (photoconductor drum 20) by laser exposure (600 dpi, not shown). As a toner carrier, a development sleeve 28 having a roughness degree Ra of 1.1 with the surface coated with a resin having a carbon black dispersed therein was used.

Figure 5:
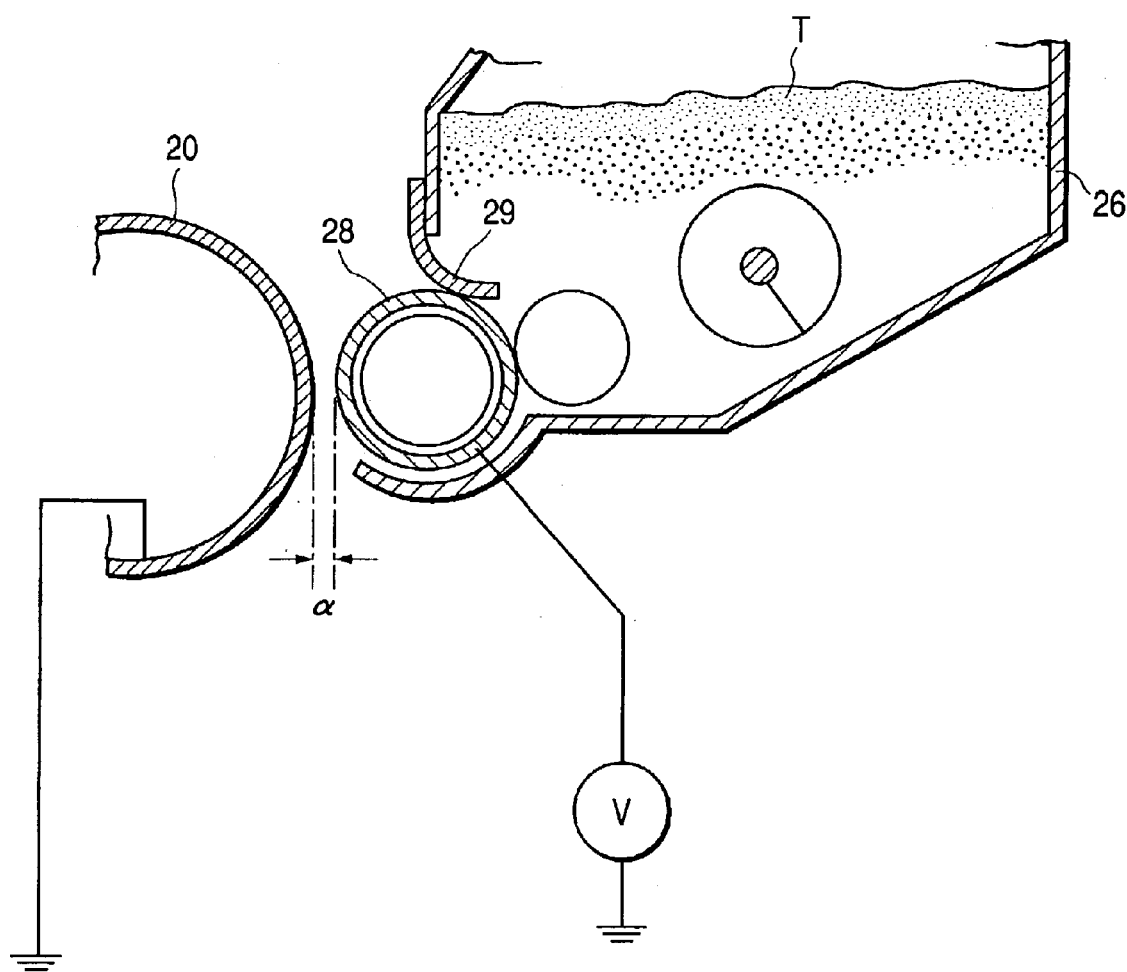
FIG. 5 is a sectional view of a principal part of a development apparatus for a one-component developer used in Examples 41 to 43 and Comparative Examples 13 to 15.

An enlarged sectional view of the principal part of the development apparatus for one-component type developers used in Examples 41 to 43 and Comparative Examples 13 to 15 is shown in FIG. 5. For conditions for developing electrostatic latent images, the speed of the development sleeve 28 was set at a speed 1.1 times as high as the movement speed of the surface of the photoconductor drum 20 opposite thereto, and the space a between the photoconductor drum 20 and the development sleeve 28 (between S and D) was 270 $\mu$m. For the member for controlling the thickness of the toner, an abutting urethane rubber blade 29 was used. In addition, the set temperature of the heat-fixation apparatus for fixing a toner image was 160° C. Furthermore, for the fixation apparatus, a fixation apparatus shown in FIGS. 6 and 7 was used.

As described above, under the condition of normal temperature and normal humidity (25° C., 60% RH), images were printed out on up to 30,000 sheets at a printout rate of 8 sheets (A4 size) per minute while the toner was supplied one after another in a continuous mode (namely, a mode in which the development device is not stopped, and thereby consumption of the toner is promoted), and the densities of resulting printout images were measured to evaluate the durability of the image according to the following criterion. In addition, the image from the 10,000 th printout was observed to make an evaluation about image fog according to the following criterion. At the same time, situations of the components constituting the image forming apparatus after the durability testing were observed to evaluate matching between each component and the above described toner. The results thereof are shown together in Table 13.

Change in Image Density During Endurance

Images were printed out on a predetermined number of normal copying papers (75 g/m$^2$), and the image density was evaluated according to the level at which the density of the image from the final printout was retained with respect to the density of the initial image. Furthermore, for the measurement of image density, a Macbeth reflective densitometer (manufactured by Macbeth Co., Ltd.) was used to measure a density relative to that of the printout image on a white ground with the density of original copy equal to 0.00.

A: Excellent (image density from the final printout is 1.40 or greater)
B: Good (image density from the final printout is 1.35 or greater and lower than 1.40)
C: Usable (image density from the final printout is 1.00 or greater and lower than 1.35)
D: Unusable (image density from the final printout is lower than 1.00)

Image Fog

Images were printed out on a predetermined number of normal copying papers (75 g/m$^2$), and the image fog was evaluated with a solid white image from the final printout. Specifically, the evaluation was made as follow: the worst value of the reflective density of the white ground after printing and the average reflective density of the paper before printing, as measured using a reflective densitometer (Reflectometer ODEL TC-6DS manufactured by Tokyo Denshoku Co., Ltd.), were defined as Ds and Dr, respectively, (Ds-Dr) was calculated from these values as a fog level to make an evaluation according to the following criterion.

A: Excellent (fog level is 0% or higher and lower than 1.5%)
B: Good (fog level is 1.5% or higher and lower than 3.0%)
C: Usable (fog level is 3.0% or higher and lower than 5.0%)
D: Unusable (fog level is 5.0% or higher)

Evaluation of Matching With Image Forming Apparatus

1. Matching with Development Sleeve

After the printout testing was completed, the situation of residual toners sticking to the surface of the development sleeve and their influence on the printout image were visually evaluated.

A: Excellent (not observed)
B: Good (almost not observed)
C: Usable (sticking residual toners are observed but the influence on the image is not significant)
D: Unusable (sticking of residual toners is significant, causing unevenness in the image)

2. Matching With Photoconductor Drum

Occurrences of scars and sticking residual toners on the surface of the photoconductor drum and their influence on the printout image were evaluated visually.

A: Excellent (not observed)
B: Good (slightly observed but no influence on the image)
C: Usable (sticking residual toners and scars are observed but the influence on the image is not significant)
D: Unusable (sticking of residual toners is significant, causing longitudinal striped defects in the image)

3. Matching with Fixation Apparatus

The surface situation of the fixation film was observed, and the results of surface characteristics and occurrences of sticking residual toners were collectively averaged to evaluate the durability of the film.

(1) Surface Characteristics

Occurrences of scares and flaking on the fixation film were visually observed and evaluated after the printout testing was completed.

A: Excellent (not observed)
B: Good (almost not observed)
C: Usable
D: Unusable (2) Situation of Sticking Toners The situation of residual toners sticking to the surface of the fixation film was visually observed and evaluated after the printout testing was completed.

A: Excellent (not observed)
B: Good (almost not observed)
C: Usable
D: Unusable

TABLE 13

| Examples | Toner | Evaluation of printout image | | | | | Evaluation of matching with other apparatus | | | |
|---|---|---|---|---|---|---|---|---|---|---|
| | | Change in image density during endurance | | | | 10 thousands fogged images | | | Fixation apparatus | |
| | | Initial | Thousand | 10 thousands | 30 thousands | | Development sleeve | Photoconductor drum | Surface characteristic | Toner fixation |
| 41 | Blue 1 | A | A | A | A | A | A | A | A | A |
| 42 | Yellow 1 | A | A | A | A | A | A | A | A | A |
| 43 | Black 1 | A | A | A | A | A | A | A | A | A |
| Comparative Example 13 | Blue 4 | C | D | D | D | D | D | D | D | D |
| Comparative Example 14 | Yellow 4 | C | D | D | D | D | D | D | D | D |
| Comparative Example 15 | Black 4 | B | C | D | D | D | D | D | D | D |

Example 44

Printout testing was performed while the blue toner (1) of Example 5 was supplied one after another in a continuous mode (namely, a mode in which the development device is not stopped, and thereby consumption of the toner is promoted) in the same manner as Example 41 except that the toner reuse mechanism of the image forming apparatus of FIG. 4 was removed and that the printout rate was set at the level of 16 sheets (A4 size) per minute. The resulting printout images and the matching with the image evaluating apparatus used were evaluated for the same items as Examples 41 to 43 and Comparative Examples 13 to 15. As a result, satisfactory results were obtained for all the items.

What is claimed is:

1. A polyhydroxyalkanoate comprising a unit of formula (1):

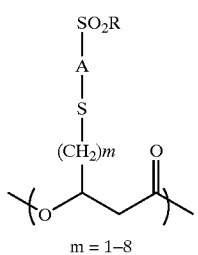

wherein R is selected from the group consisting of OH, a halogen atom, ONa, OK, $OCH_3$ and $OC_2H_5$; A represents a substituted or unsubstituted aliphatic hydrocarbon structure; m is an integer number selected from 1 to 8; and in the case where a plurality of units exist in the same molecule, R, A and m in one unit can be different from them in another unit respectively.

2. The polyhydroxyalkanoate according to claim 1, comprising a unit of formula (2):

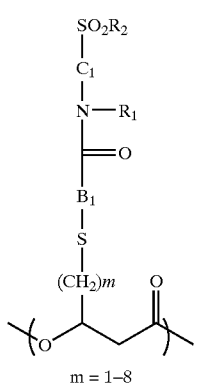

wherein $R_1$ is H or $CH_3$; $R_2$ is selected from the group consisting of OH, a halogen atom, ONa, OK, $OCH_3$ and $OC_2H_5$; $B_1$ and $C_1$ each represent a substituted or unsubstituted aliphatic hydrocarbon structure; m is an integer number selected from 1 to 8; and in the case where a plurality of units exist in the same molecule, $R_1$, $R_2$, $B_1$, $C_1$ and m in one unit can be different from them in another unit respectively.

3. The polyhydroxyalkanoate according to claim 2, comprising a unit of formula (3):

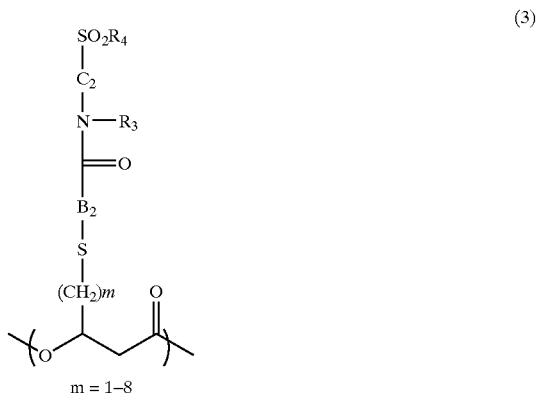

wherein $R_3$ is H or $CH_3$; $R_4$ is selected from the group consisting of OH, a halogen atom, ONa, OK, $OCH_3$ and $OC_2H_5$; $B_2$ and $C_2$ each represent a straight-chain or branched alkylene group having 1 to 8 carbon atoms; m is an integer number selected from 1 to 8; and in the case where a plurality of units exist in the same molecule, $R_3$, $R_4$, $B_2$, $C_2$ and m in one unit can be different from them in another unit respectively.

4. The polyhydroxyalkanoate according to claim 3, comprising a unit of formula (4):

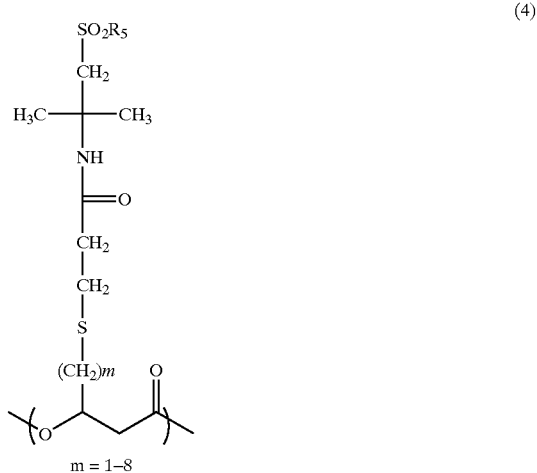

wherein $R_5$ is selected from the group consisting of OH, a halogen atom, ONa, OK, $OCH_3$ and $OC_2H_5$; m is an integer number selected from 1 to 8; and in the case where a plurality of units exist in the same molecule, $R_5$ and m in one unit can be different from them in another unit respectively.

5. The polyhydroxyalkanoate according to claim 1, wherein m in formula (1) is an integer selected from the group consisting of 4, 6 and 8.

6. The polyhydroxyalkanoate according to claim 1, wherein m in formula (1) is an integer of 3 or 5.

7. The polyhydroxyalkanoate according to claim 1, comprising at least one of a 3-hydroxy-ω-alkanoic acid unit of formula (5):

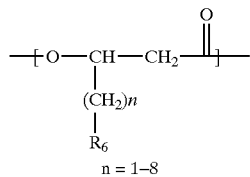
(5)

n = 1–8 wherein n is an integer number selected from 1 to 8; $R_6$ contains a residue having a phenyl structure or a thienyl structure; and in the case where a plurality of units exist in the same molecule, n and $R_6$ in one unit can be different from them in another unit respectively and a 3-hydroxy-ω-cyclohexylalkanoic acid unit of formula (6):

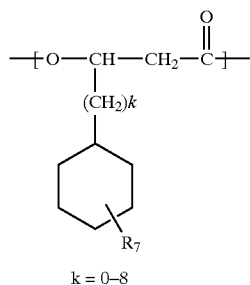
(6)

k = 0–8 wherein $R_7$ is a substituent group in the cyclohexyl group selected from the group consisting of H, CN, $NO_2$, a halogen atom, $CH_3$, $C_2H_5$, $C_3H_7$, $CF_3$, $C_2F_5$ and $C_3F_7$; k is an integer number selected from 0 to 8; and in the case where a plurality of units exist in the same molecule, k and $R_7$ in one unit can be different from them in another unit respectively.

8. The polyhydroxyalkanoate according to claim 7, wherein $R_6$ in formula (5) is selected from the group consisting of the groups of the following formulas (7), (8), (9), (10), (11), (12), (13), (14), (15), (16) and (17):

unsubstituted or substituted phenyl groups of formula (7):

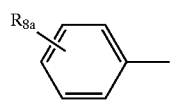
(7)

wherein $R_{8a}$ represents a substituent group in the aromatic ring selected from the group consisting of H, a halogen atom, CN, $NO_2$, $CH_3$, $C_2H_5$, $C_3H_7$, $CH=CH_2$, $COOR_{8b}$ ($R_{8b}$ represents any one selected from the group consisting of H, Na and K), $CF_3$, $C_2F_5$ and $C_3F_7$, and in the case where a plurality of units exist in the same molecule, $R_{8a}$ in one unit can be different from that in another unit;

unsaturated or saturated phenoxy groups of formula (8):

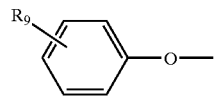
(8)

wherein $R_9$ represents a substituent group in the aromatic ring selected from the group consisting of H, a halogen atom, CN, $NO_2$, $CH_3$, $C_2H_5$, $C_3H_7$, $SCH_3$, $CF_3$, $C_2F_5$ and $C_3F_7$, and in the case
where a plurality of units exist in the same molecule $R_9$ in one unit can be different from that in another unit;

unsubstituted or substituted benzoyl groups each of formula (9):

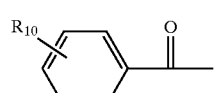
(9)

wherein $R_{10}$ represents a substituent group in the aromatic ring selected from the group consisting of H, a halogen atom, CN, $NO_2$, $CH_3$, $C_2H_5$, $C_3H_7$, $CF_3$, $C_2F_5$ and $C_3F_7$, and in the case where a plurality of units exist in the same molecule $R_{10}$ in one unit can be different from that in another unit;

unsubstituted or substituted phenylsulfanyl groups of formula (10):

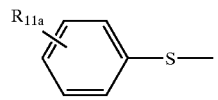
(10)

wherein $R_{11a}$ represents a substituent group in the aromatic ring selected from the group consisting of H, a halogen atom, CN, $NO_2$, $COOR_{11b}$, $SO_2R_{11c}$ ($R_{11b}$ represents any one selected from the group consisting of H, Na, K, $CH_3$ and $C_2H_5$, and $R_{11c}$ represents any one selected from the group consisting of OH, ONa, OK, a halogen atom, $OCH_3$ and $OC_2H_5$), $CH_3$, $C_2H_5$, $C_3H_7$, $(CH_3)_2$—CH and $(CH_3)_3$—C, and in the case where a plurality of units exist in the same molecule $R_{11a}$ in one unit can be different from that in another unit;

unsubstituted or substituted (phenylmethyl) sulfanyl groups of formula (11):

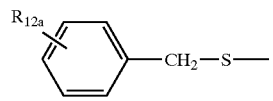
(11)

wherein $R_{12a}$ represents a substituent group in the aromatic ring selected from the group consisting of H, a halogen atom, CN, $NO_2$, $COOR_{12b}$, $SO_2R_{12c}$ ($R_{12b}$ represents any one selected from the group consisting of H, Na, K, $CH_3$ and $C_2H_5$, and $R_{12c}$ represents any one selected from the group consisting of OH, ONa, OK, a halogen atom, $OCH_3$ and $OC_2H_5$), $CH_3$, $C_2H_5$, $C_3H_7$, $(CH_3)_2$—CH and $(CH_3)_3$—C, and in the case where a plurality of units exist in the same molecule $R_{12a}$ in one unit can be different from that in another unit;

2-thienyl group of formula (12):

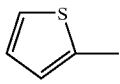
(12)

2-thienylsulfanyl group of formula (13):

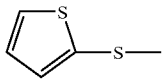
(13)

2-thienylcarbonyl group of formula (14):

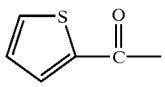
(14)

unsubstituted or substituted phenylsulfinyl groups of formula (15):

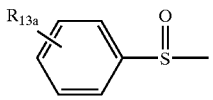
(15)

wherein $R_{13a}$ represents a substituent group in the aromatic ring selected from the group consisting of H, a halogen atom, CN, $NO_2$, $COOR_{13b}$ ($R_{13b}$ represents any one selected from the group consisting of H, Na, K, $CH_3$ and $C_2H_5$), $SO_2R_{13c}$ ($R_{13c}$ represents any one selected from the group consisting of OH, ONa, OK, a halogen atom, $OCH_3$ and $OC_2H_5$), $CH_3$, $C_2H_5$, $C_3H_7$, $(CH_3)_2$—CH and $(CH_3)_3$—C, and in the case where a plurality of units exist in the same molecule $R_{13a}$ in one unit can be different from that in another unit;

unsubstituted or substituted phenylsulfonyl groups of formula (16):

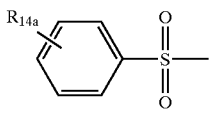
(16)

wherein $R_{14a}$ represents a substituent group in the aromatic ring selected from the group consisting of H, a halogen atom, CN, $NO_2$, $COOR_{14b}$ ($R_{14b}$ represents any one selected from the group consisting of H, Na, K, $CH_3$ and $C_2H_5$), $SO_2R_{14c}$ ($R_{14c}$ represents any one selected from the group consisting of OH, ONa, OK, a halogen atom, $OCH_3$ and $OC_2H_5$), $CH_3$, $C_2H_5$, $C_3H_7$, $(CH_3)_2$—CH and $(CH_3)_3$—C, and in the case where a plurality of units exist in the same molecule $R_{14a}$ in one unit can be differend from that in another unit; and (phenylmethyl)oxy groups of formula (17):

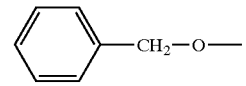
(17)

and in the case where a plurality of units exist in the same molecule, $R_6$ in one unit of formula (5) can be different from that in another unit.

9. The polyhydroxyalkanoate according to claim 1, wherein the number-average molecular weight is in the range of from 1000 to 1000000.

10. A method of producing polyhydroxyalkanoate comprising a unit of formula (1):

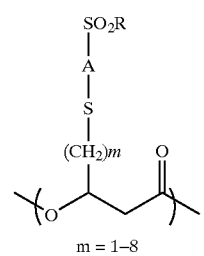
(1)

m = 1–8 wherein R is selected from the group consisting of OH, a halogen atom, ONa, OK, $OCH_3$ and $OC_2H_5$, A represents a substituted or unsubstituted aliphatic hydrocarbon structure; m is an integer number selected from 1 to 8; and in the case where a plurality of units exist in the same molecule, R, A and m in one unit can be different from them in another unit respectively, which comprises the step of:

reacting a polyhydroxyalkanoate comprising a unit of formula (18):

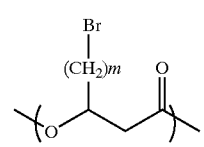
(18)

wherein m is an integer number selected from 1 to 8, and in the case where a plurality of units exist in the same molecule, m in one unit can be different from that in another unit, with at least one type of compounds of formula (19):

$HS-A_1-SO_2R_{15}$ (19)

wherein $R_{15}$ is selected from the group consisting of OH, a halogen atom, ONa, OK, $OCH_3$ and $OC_2H_5$ and $A_1$ is a substituted or unsubstituted aliphatic hydrocarbon structure, and in the case where a plurality of types of compounds exist in the same molecule, $R_{15}$ and $A_1$ in one unit can be different from them in another unit respectively.

11. A method of producing polyhydroxyalkanoate comprising a unit of formula (2):

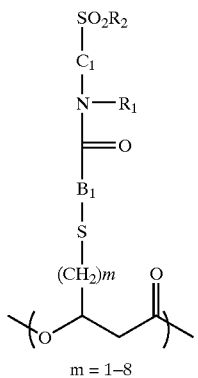
(2)

m = 1–8 wherein $R_1$ is H or $CH_3$; $R_2$ is selected from the group consisting of OH, a halogen atom, ONa, OK, $OCH_3$ and $OC_2H_5$; $B_1$ and $C_1$ represent a substituted or unsubstituted aliphatic hydrocarbon structure; m is an integer number selected from 1 to 8; and in the case where a plurality of units exist in the same molecule, $R_1$, $R_2$, $B_1$, $C_1$ and m in one unit can be different from them in another unit respectively, which comprises the step of:

reacting a polyhydroxyalkanoate comprising a unit of formula (18):

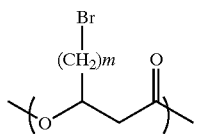
(18)

wherein m is an integer number selected from 1 to 8, and in the case where a plurality of units exist in the same molecule, m in one unit can be different from that in another unit, with at least one type of compounds of formula (20):

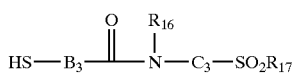
(20)

wherein $R_{16}$ is H or $CH_3$; $R_{17}$ is selected from the group consisting of OH, a halogen atom, ONa, OK, $OCH_3$ and $OC_2H_5$; $B_3$ and $C_3$ are selected from substituted or unsubstituted aliphatic hydrocarbon structures; and in the case where a plurality of types of compounds exist in the same molecule, $R_{16}$, $R_{17}$, $B_3$ and $C_3$ in one unit can be different from them in another unit respectively.

12. The method according to claim 10, wherein the reacting step is carried out under basic condition.

13. The method according to claim 12, wherein at least one selected from the group consisting of dimetylamine, diethylamine, trimethylamine, triethylamine, dibutylamine, morpholine, piperidine, sodium hydride, sodium hydroxide, potassium hydroxide, sodium carbonate, potassium carbonate, sodium methylate and sodium ethylate is used as a basic catalyst in the reacting step.

14. In a charge controlling agent controlling the charged state of powder, the improvement which comprises a charge controlling agent containing polyhydroxyalkanoate comprising a unit of formula (1):

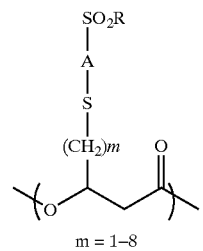
(1)

m = 1–8 wherein R is selected from the group consisting of OH, a halogen atom, ONa, OK, $OCH_3$ and $OC_2H_5$; A represents a substituted or unsubstituted aliphatic hydrocarbon structure; m is an integer number selected from 1 to 8; and in the case where a plurality of units exist in the same molecule, R, A and m in one unit can be different from them in another unit respectively.

15. The charge controlling agent controlling the charged state of powder according to claim 14, the charge controlling agent containing polyhydroxyalkanoate comprising a unit of formula (2):

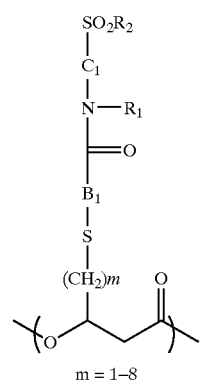
(2)

m = 1–8 wherein $R_1$ is H or $CH_3$; $R_2$ is selected from the group consisting of OH, a halogen atom, ONa, OK, $OCH_3$ and $OC_2H_5$; $B_1$ and $C_1$ each represent a substituted or unsubstituted aliphatic hydrocarbon structure; m is an integer number selected from 1 to 8; and in the case where a plurality of units exist in the same molecule, $R_1$, $R_2$, $B_1$, $C_1$ and m in one unit can be different from them in another unit respectively.

16. The charge controlling agent controlling the charged state of powder according to claim 15, the charge controlling agent containing polyhydroxyalkanoate comprising a unit of formula (3):

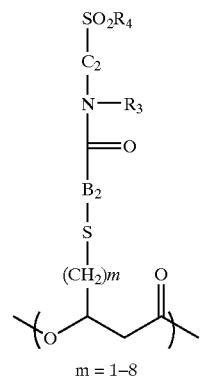
(3)

m = 1–8 wherein $R_3$ is H or $CH_3$; $R_4$ is selected from the group consisting of OH, a halogen atom, ONa, OK, $OCH_3$ and OC$_2$H$_5$; B$_2$ and C$_2$ each represent a straight-chain or branched alkylene group having 1 to 8 carbon atoms; m is an integer number selected from 1 to 8; and in the case where a plurality of units exist in the same molecule, R$_3$, R$_4$, B$_2$, C$_2$ and m in one unit can be different from them in another unit respectively.

17. The charge controlling agent controlling the charged state of powder according to claim 16, the charge controlling agent containing polyhydroxyalkanoate comprising a unit of formula (4):

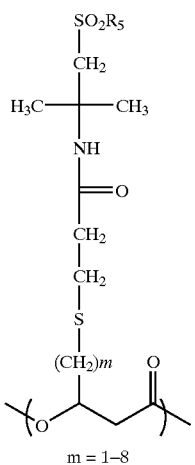
(4)

m = 1–8 wherein R$_5$ is selected from the group consisting of OH, a halogen atom, ONa, OK, OCH$_3$ and OC$_2$H$_5$; m is an integer number selected from 1 to 8; and in the case where a plurality of units exist in the same molecule, R$_5$ and m in one unit can be different from them in another unit respectively.

18. The charge controlling agent according to claim 14, comprising at least one of
a 3-hydroxy-w-alkanoic acid unit of formula (5):

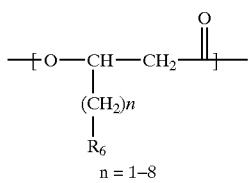
(5)

n = 1–8 wherein n is an integer number selected from 1 to 8; R$_6$ contains a residue having a phenyl structure or a thienyl structure; and in the case where a plurality of units exist in the same molecule, n and R$_6$ in one unit can be different from them in another unit respectively and
a 3-hydroxy-w-cyclohexylalkanoic acid unit of formula (6):

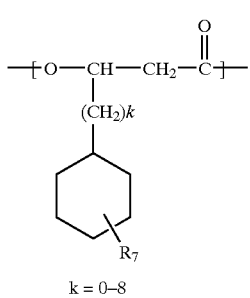
(6)

k = 0–8 wherein R$_7$ is a substituent group in the cyclohexyl group selected from the group consisting of H, CN, NO$_2$, a halogen atom, CH$_3$, C$_2$H$_5$, C$_3$H$_7$, CF$_3$, C$_2$F$_5$ and C$_3$F$_7$; k is an integer number selected from 0 to 8; and in the case where a plurality of units exist in the same molecule, k and R$_7$ in one unit can be different from them in another unit respectively.

19. The charge controlling agent according to claim 18, wherein R$_6$ in chemical formula (5) is selected from the group consisting of the groups of the following formulas (7), (8), (9), (10), (11), (12), (13), (14), (15), (16) and (17):

unsubstituted or substituted phenyl groups of formula (7):

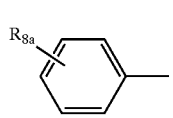
(7)

wherein R$_{8a}$ represents a substituent group in the aromatic ring selected from the group consisting of H, a halogen atom, CN, NO$_2$, CH$_3$, C$_2$H$_5$, C$_3$H$_7$, CH=CH$_2$, COOR$_{8b}$ (R$_{8b}$ represents any one selected from the group consisting of H, Na and K), CF$_3$, C$_2$F$_5$ and C$_3$F$_7$, and in the case where a plurality of units exist in the same molecule, R$_{8a}$ in one unit can be different from that in another unit;

unsaturated or saturated phenoxy groups of formula (8):

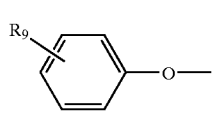
(8)

wherein R$_9$ represents a substituent group in the aromatic ring selected from the group consisting of H, a halogen atom, CN, NO$_2$, CH$_3$, C$_2$H$_5$, C$_3$H$_7$, SCH$_3$, CF$_3$, C$_2$F$_5$ and C$_3$F$_7$, and in the case where a plurality of units exist in the same molecule, R$_9$ in one unit can be different from that in another unit;

unsubstituted or substituted benzoyl groups each of formula (9):

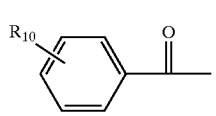
(9)

wherein R$_{10}$ represents a substituent group in the aromatic ring selected from the group consisting of H, a halogen atom, CN, NO$_2$, CH$_3$, C$_2$H$_5$, C$_3$H$_7$, CF$_3$, C$_2$F$_5$ and C$_3$F$_7$, and in the case where a plurality of units exist in the same molecule, R$_{10}$ in one unit can be different from that in another unit;

unsubstituted or substituted phenylsulfanyl groups of formula (10):

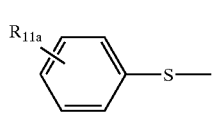
(10)

wherein R$_{11a}$ represents a substituent group in the aromatic ring selected from the group consisting of H, a halogen atom, CN, NO$_2$, COOR$_{11b}$, SO$_2$R$_{11c}$ (R$_{11b}$ represents any one selected from the group consisting of H, Na, K, CH$_3$ and C$_2$H$_5$, and R$_{11c}$ represents any one selected from the group consisting of OH, ONa, OK, a halogen atom, OCH$_3$ and OC$_2$H$_5$), CH$_3$, C$_2$H$_5$, $C_3H_7$, $(CH_3)_2$—CH and $(CH_3)_3$—C, and in the case where a plurality of units exist in the same molecule, $R_{11a}$ in one unit can be different from that in another unit;

unsubstituted or substituted (phenylmethyl) sulfanyl groups of formula (11):

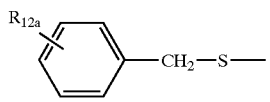
(11)

wherein $R_{12a}$ represents a substituent group in the aromatic ring selected from the group consisting of H, a halogen atom, CN, $NO_2$, $COOR_{12b}$, $SO_2R_{12c}$ ($R_{12b}$ represents any one selected from the group consisting of H, Na, K, $CH_3$ and $C_2H_5$, and $R_{12c}$ represents any one selected from the group consisting of OH, ONa, OK, a halogen atom, $OCH_3$ and $OC_2H_5$), $CH_3$, $C_2H_5$, $C_3H_7$, $(CH_3)_2$—CH and $(CH_3)_3$—C, and in the case where a plurality of units exist in the same molecule $R_{12a}$ in one unit can be different from that in another unit;

2-thienyl group of formula (12):

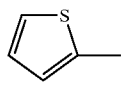
(12)

2-thienylsulfanyl group of formula (13):

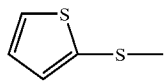
(13)

2-thienylcarbonyl group of formula (14):

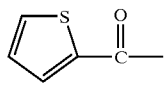
(14)

unsubstituted or substituted phenylsulfinyl groups of formula (15):

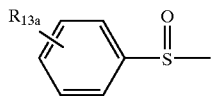
(15)

wherein $R_{13a}$ represents a substituent group in the aromatic ring selected from the group consisting of H, a halogen atom, CN, $NO_2$, $COOR_{13b}$ ($R_{13b}$ represents any one selected from the group consisting of H, Na, K, $CH_3$ and $C_2H_5$), $SO_2R_{13c}$ ($R_{13c}$ represents any one selected from the group consisting of OH, ONa, OK, a halogen atom, $OCH_3$ and $OC_2H_5$), $CH_3$, $C_2H_5$, $C_3H_7$, $(CH_3)_2$—CH and $(CH_3)_3$—C, and in the case where a plurality of units exist in the same molecule $R_{13a}$ in one unit can be different from that in another unit;

unsubstituted or substituted phenylsulfonyl groups of formula (16):

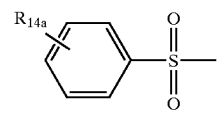
(16)

wherein $R_{14a}$ represents a substituent group in the aromatic ring selected from the group consisting of H, a halogen atom, CN, $NO_2$, $COOR_{14b}$, ($R_{14b}$ represents any one selected from the group consisting of H, Na, K, $CH_3$ and $C_2H_5$), $SO_2R_{14c}$ ($R_{14c}$ represents any one selected from the group consisting of OH, ONa, OK, a halogen atom, $OCH_3$ and $OC_2H_5$), $CH_3$, $C_2H_5$, $C_3H_7$, $(CH_3)_2$—CH and $(CH_3)_3$—C, and in the case where a plurality of units exist in the same molecule $R_{14a}$ in one unit can be differend from that in another unit; and (phenylmethyl)oxy groups of formula (17):

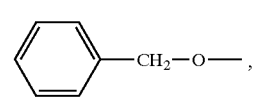
(17)

and in the case where a plurality of units exist in the same molecule, $R_6$ in one unit can be different from that in another unit.

20. The charge controlling agent according to claim 14, wherein said powder is an electrostatic latent image developing toner.

21. The charge controlling agent according to claim 14, wherein the number-average molecular weight of said polyhydroxyalkanoate is in the range of from 1000 to 1000000.

22. A toner binder for use in an electrostatic latent image developing toner, the toner binder containing the charge controlling agent according to claim 14.

23. An electrostatic latent image developing toner containing a binder resin, a coloring agent and the charge controlling agent according to claim 14.

24. A method for forming an image which comprises the steps of:

applying a voltage to an electrification member from the outside to electrify an electrostatic latent image carrier, forming an electrostatic latent image on the electrified electrostatic latent image carrier, developing the electrostatic latent image by an electrostatic latent image developing toner to form a toner image on the electrostatic latent image carrier, transferring the toner image on the electrostatic latent image carrier to a record material, and fixing the toner image on the record material by heat, wherein an electrostatic latent image developing toner according to claim 23 is used.

25. The method according to claim 24, wherein said transferring step comprises a first transferring step of transferring the toner image on the electrostatic latent image carrier to an intermediate transfer body and a second transferring step of transferring the toner image on the intermediate transfer body to the record material.

26. An image forming apparatus comprising a means for applying a voltage to an electrification member from the outside to electrify an electrostatic latent image carrier, a means for forming an electrostatic latent image on the electrified electrostatic latent image carrier, a means for developing the electrostatic latent image by an electrostatic latent image developing toner to form a toner image on the electrostatic latent image carrier, a means for transferring the toner image on the electrostatic latent image carrier to a record material, and a means for fixing the toner image on the record material by heat, wherein an electrostatic latent image developing toner according to claim 23 is used.

27. The image forming apparatus according to claim 26, wherein said transferring means comprises a first transferring means for transferring the toner image on the electrostatic latent image carrier to an intermediate transfer body and a second transferring means for transferring the toner image on the intermediate transfer body to the record material.

* * * * *

UNITED STATES PATENT AND TRADEMARK OFFICE
CERTIFICATE OF CORRECTION

PATENT NO. : 6,908,721 B2
DATED : June 21, 2005
INVENTOR(S) : Takashi Kenmoku et al.

It is certified that error appears in the above-identified patent and that said Letters Patent is hereby corrected as shown below:

Title page,
Item [54], Title, "POLYHYDROXYALKANOATE HAVING AMIDE GROUP AND SULFONIC GROUP, METHOD OF PRODUCING THE SAME, CHARGE CONTROLLING AGENT CONTAINING NOVEL POLYHYDROXYALAKNAOTE, TONER BINDER, TONER, AND IMAGE FORMING APPARATUS USING THE TONER" should read
-- POLYHYDROXYALKANOATE HAVING AMIDE GROUP AND SULFONIC GROUP, METHOD OF PRODUCING THE SAME, CHARGE CONTROLLING AGENT CONTAINING POLYHYDROXYALKANOATE, TONER BINDER, TONER, AND IMAGE FORMING APPARATUS USING THE TONER --.

Item [56], References Cited, OTHER PUBLICATIONS,
"Kim" reference, "Incorportion" should read -- Incorporation --;
"Gross" reference, "Biodengradabil-" should read -- Biodegradabil- --;
"Aróstegui" reference, "Marcomolecules" should read -- Macromolecules --; and
"Constantin" reference, "hydroxyalkanoates)." should read -- hydroxyalkanoates. --.

Column 1,
Line 5, "NOVEL" should be deleted; and
Line 6, "POLYHYDROXYALAKNAOTE" should read
-- POLYHYDROXYALKANOATE --.

Column 3,
Line 6, "may various" should read -- may be in various --;
Line 41, "requites" should read -- balls --; and
Line 56, "of" (first occurrence) should be deleted.

Column 4,
Line 16, "11-pheoxyundecanoic" should read -- 11-phenoxyundecanoic --; and
Line 41, "Pseudomonas oleovorans" should be italicized.

Column 5,
Lines 12 and 30, "(e.g." should read -- (e.g., --; and
Line 35, "an" should read -- a --.

Column 6,
Line 38, "3-hydroxybutylic" should read -- 3-hydroxybutyric --.

Column 7,
Line 31, "ane" should read -- and --.

UNITED STATES PATENT AND TRADEMARK OFFICE
CERTIFICATE OF CORRECTION

PATENT NO. : 6,908,721 B2
DATED : June 21, 2005
INVENTOR(S) : Takashi Kenmoku et al.

It is certified that error appears in the above-identified patent and that said Letters Patent is hereby corrected as shown below:

Column 11,
Line 32, "molecule" should read -- molecule, --;
Line 46, "$SO_2R_{14b}$" should read -- $SO_2R_{14c}$ --;
Line 50, "molecule" should read -- molecule, --; and
Line 51, "differend" should read -- different --.

Column 12,
Line 45, "dimetylamine," should read -- dimethylamine, --.

Column 15,
Line 17, "Bioscene" should read -- Bioscience --; and
Line 61, "an" should read -- a --.

Column 17,
Line 18, "3-hydroxy-ω-bromoalakanoic" should read -- 3-hydroxy-ω-bromoalkanoic --;
Line 22, "accumulation the" should read -- accumulation of the --; and
Line 34, "in stead" should read -- instead -- (close up space).

Column 18,
Line 36, "respectively." should read -- respectively). --.

Column 20,
Line 46, "mechanchmically" should read -- mechanochemically --.

Column 21,
Line 52, "salcylate," should read -- salicylate, --.

Column 22,
Line 11, "clearly" should read -- to clearly --.

Column 23,
Line 38, "bibasic" should read -- dibasic --.

Column 25,
Line 63, "may widely" should read -- may be widely --.

Column 27,
Line 42, "hydrophobility" should read -- hydrophobicity --; and
Line 47, "agent" should read -- agents --.

UNITED STATES PATENT AND TRADEMARK OFFICE
CERTIFICATE OF CORRECTION

PATENT NO. : 6,908,721 B2
DATED : June 21, 2005
INVENTOR(S) : Takashi Kenmoku et al.

It is certified that error appears in the above-identified patent and that said Letters Patent is hereby corrected as shown below:

Column 28,
Line 19, "are" should read -- is --.

Column 29,
Lines 13 and 15, "bases" should read -- basis --; and
Line 26, "an" should read -- a --.

Column 30,
Line 42, "an" should read -- a --.

Column 42,
Line 28, "part" should read -- parts --.

Column 43,
Line 59, "Examples 0.8" should read -- Examples 8 --.

Column 45,
Line 44, "stylene-butylacrylate" should read -- styrene-butylacrylate --.

Column 48,
Line 58, "terephtalic" should read -- terephthalic --.

Column 52,
Line 16, "follow:" should read -- follows: --; and
Line 48, "scares" should read -- scars --.

Column 55,
Line 28, "follow:" should read -- follows: --.

Column 56,
Line 27, "scares" should read -- scars --.

Column 60,
Lines 11-12, "case ¶ where" should read -- case where -- (close up space); and
Lines 12, 27, 45 and 65, "molecule" should read -- molecule, --.

Column 61,
Lines 45 and 66, "molecule" should read -- molecule, --; and
Line 67, "differend" should read -- different --.

UNITED STATES PATENT AND TRADEMARK OFFICE
CERTIFICATE OF CORRECTION

PATENT NO. : 6,908,721 B2
DATED : June 21, 2005
INVENTOR(S) : Takashi Kenmoku et al.

It is certified that error appears in the above-identified patent and that said Letters Patent is hereby corrected as shown below:

Column 62,
Line 31, "$OC_2H_5$," should read -- $OC_2H_5$; --.

Column 63,
Line 58, "dimetylamine," should read -- dimethylamine, --.

Column 65,
Line 36, "3-hydroxy-w-alkanoic" should read -- 3-hydroxy-ω-alkanoic --; and
Line 51, "3-hydroxy-w-cyclohexylalkanoic" should read -- 3-hydroxy-ω-cyclohexylalkanoic --.

Column 67,
Lines 22 and 64, "molecule" should read -- molecule, --.

Column 68,
Line 17, "molecule" should read -- molecule, --; and
Line 18, "differend" should read -- different --.

Signed and Sealed this

Eighth Day of November, 2005

JON W. DUDAS
*Director of the United States Patent and Trademark Office*